US008546140B2

(12) United States Patent \
Mack et al.

(10) Patent No.: US 8,546,140 B2 \
(45) Date of Patent: Oct. 1, 2013

(54) METHODS FOR THE PRODUCTION OF IPS CELLS USING NON-VIRAL APPROACH

(75) Inventors: Amanda Mack, Madison, WI (US); James Thomson, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 268 days.

(21) Appl. No.: 12/478,154

(22) Filed: Jun. 4, 2009

(65) Prior Publication Data

US 2010/0003757 A1 Jan. 7, 2010

Related U.S. Application Data

(60) Provisional application No. 61/058,858, filed on Jun. 4, 2008, provisional application No. 61/160,584, filed on Mar. 16, 2009.

(51) Int. Cl.
| | | |
|---|---|---|
| *C12N 5/00* | (2006.01) | |
| *C12N 5/02* | (2006.01) | |
| *C12N 5/071* | (2010.01) | |
| *C12N 15/00* | (2006.01) | |
| *C12N 15/86* | (2006.01) | |

(52) U.S. Cl.
USPC ............ 435/377; 435/366; 435/455; 435/456

(58) Field of Classification Search
USPC .................................. 435/377, 366, 455, 456
See application file for complete search history.

(56) References Cited

U.S. PATENT DOCUMENTS

| | | | |
|---|---|---|---|
| 7,465,580 B2 | 12/2008 | Sugden et al. | 435/320.1 |
| 8,058,065 B2 * | 11/2011 | Yamanaka et al. | 435/377 |
| 2005/0079616 A1 * | 4/2005 | Reubinoff | 435/456 |
| 2005/0260564 A1 * | 11/2005 | Sugden et al. | 435/5 |
| 2006/0160218 A1 * | 7/2006 | Slack et al. | 435/455 |
| 2008/0003560 A1 | 1/2008 | Nakatsuji et al. | 435/1.1 |
| 2008/0233610 A1 | 9/2008 | Thomson et al. | 435/320.1 |
| 2010/0184227 A1 | 7/2010 | Thomson et al. | 435/455 |

FOREIGN PATENT DOCUMENTS

| | | |
|---|---|---|
| EP | 2 072 618 A | 6/2009 |
| WO | WO 2009/032194 | 3/2009 |
| WO | WO 2009/032456 | 3/2009 |
| WO | WO 2009/091543 | 7/2009 |

OTHER PUBLICATIONS

Baker. Nature Reports Stem Cells, pp. 1-2, published online Jun. 7, 2007, accessed online at http://www.nature.com/stemcells/2007/0706/070607/full/stemcells.2007.9.html on Oct. 18, 2012.*
"pMX-STAT5A(1*6) Retroviral Vector," *Cell BioLabs, Inc.*, available at http://www.cellbiolabs.com, 2008.
Almqvist et al., "Functional interaction of Oct transcription factors with the family of repeats in Epstein-Barr virus oriP," *J. of General Virology*, 86 (Part 5): 1261-1267, 2005.
Altmann et al., "Transcriptional activation by EBV nuclear antigen 1 is essential for the expression of EBV's transforming genes," *PNAS*, 103(38):14188-14193, 2006.
Baer et al., "Transcriptional properties of genomic transgene integration sites marked by electroporation or retroviral infection," *Biochemistry*, 39:7041-7049, 2000.
Baker, "Reprogramming kinetics," *Nature Reports Stem Cells*, available at http://www.nature.com/stemcells/2008/0803/080306/full/stemcells.2008.44.html, published online Mar. 6, 2008.
Bingham, "Cosuppression comes to the animals," *Cell*, 90(3):385-387, 1997.
Bode et al., "The hitchhiking principle: Optimizing episomal vectors for the use in gene therapy and biotechnology," *Gene Ther. Mol. Biol.*, 6:33-46, 2001.
Bode et al., "The transgeneticist's toolbox: novel methods for the targeted modification of eukaryotic genomes," *Biol. Chem.*, 381:801-813, 2000b.
Boyer et al., "Core transcriptional regulatory circuitry in human embryonic stem cells," *Cell*, 122(6):947-56, 2005.
Brambrink et al., "Sequential expression of pluripotency markers during direct reprogramming of mouse somatic cells," *Cell Stem Cell*, 7(2):151-159, 2008.
Calos et al., "Stability without a centromere," *PNAS*, 95:4084-4085, 1998.
Garrick et al., "Repeat-induced gene silencing in mammals," *Nat. Genet.*, 18:56-59, 1998.
Hung et al., "Maintenance of Epstein-Barr virus (EBV) *ori*P-based episomes requires EBV-encoded nuclear antigen-1 chromosome-binding domains, which can be replaced by high-mobility group-I or histone H1," *PNAS*, 98(4):1865-1870, 2001.
International Search Report and Written Opinion, issued in Int. App. No. PCT/US2009/046209, mailed Sep. 8, 2009.
Jenke et al., "Nuclear scaffold/matrix attached region modules linked to a transcription unit are sufficient for replication and maintenance of a mammalian episome," *PNAS*, 101 (31), 11322-11327, 2004.
Kennedy and Sugden, "EBNA-1, a bifunctional transcriptional activator," *Mol. and Cell. Biol.*, 23(19):6901-6908, 2003.
Kennedy et al., "Epstein-Barr virus provides a survival factor to Burkitt's lymphomas," *PNAS*, 100:14269-14274, 2003.
Leight and Sugden, "Establishment of an *ori*P replicon is dependent upon an infrequent, epigenetic event," *Mol. and Cell. Biol.*, 21(13):4149-4161, 2001.
Lewitzky and Yamanaka, "Reprogramming somatic cells towards pluripotency by defined factors," *Current Opinion in Biotechnology*, 18:467-473, 2007.
Lindner and Sugden, "The plasmid replicon of Epstein-Barr virus: mechanistic insights into efficient licensed, extrachromosomal replication in human cells," *Plasmid*, 58 (1): 1-12, 2007.
Mackey and Sugden, "The linking regions of EBNA 1 are essential for its support of replication and transcription," *Mol. Cell. Biol.*, 19(5):3349-3359, 1999.
Manzini et al., "Genetically modified pigs produced with a nonviral episomal vector," *PNAS*, 103(47):17672-17677, 2006.

(Continued)

*Primary Examiner* — Thaian N Ton \
(74) *Attorney, Agent, or Firm* — Parker Highlander PLLC

(57) ABSTRACT

Methods and composition of induction of pluripotent stem cells and other desired cell types are disclosed. For example, in certain aspects methods for generating essentially vector-free induced pluripotent stem cells are described. Furthermore, the invention provides induced pluripotent stem cells and desired cell types essentially free of exogenous vector elements with the episomal expression vectors to express differentiation programming factors.

5 Claims, 5 Drawing Sheets

(56) References Cited

OTHER PUBLICATIONS

Nanbo et al., "The coupling of synthesis and partitioning of EBV's plasmid replicon is revealed in live cells," *The EMBO Journal*, 26(19):4252-4562, 2007.

Piechaczek et al., "A vector based on the SV40 origin of replication and chromosomal S/MARs replicates episomally in CHO cells," *Nucleic Acids Res.*, 27(2):426-428, 1999.

Ren et al., "Establishment and applications of Epstein-Barr virus-based episomal vectors in human embryonic stem cells," *Stem Cells*, 24 (5): 2006, pp. 1338-1347.

Schaarschmidt et al., "An episomal mammalian replicon: sequence-independent binding of the origin recognition complex," *EMBO J.*, 23(1):191-201, .2004.

Sears et al., "The amino terminus of Epstein-Barr Virus (EBV) nuclear antigen 1 contains AT hooks that facilitate the replication and partitioning of latent EBV genomes by tethering them to cellular chromosomes," *J. Virol.*, 78(21):11487-11505, 2004.

Stadtfeld et al., "Defining molecular cornerstones during fibroblast to iPS cell reprogramming in mouse," *Cell Stem Cell*, 2:230-240, 2008.

Stojkovic and Phinney, "Programming battle: egg vs. virus," *Stem Cells Express*, available online at http://stemcells.alphamedpress.org/cgi/content/full/26/1/1 , Nov. 29, 2007.

Takahashi et al., "Induction of pluripotent stem cells from adult human fibroblasts by defined factors ," *Cell*, 131(5):861-72, 2007.

Takahashi et al., "Induction of pluripotent stem cells from mouse embryonic and adult fibroblast cultures by defined factors," *Cell*, 126(4):663-676, 2006.

Yates et al., "A cis-acting element from the Epstein-Barr viral genome that permits stable replication of recombinant plasmids in latently infected cells," *Proc. Natl. Acad. Sci. USA*, 81:3806-3810, 1984.

Yates et al., "Stable replication of plasmids derived from Epstein-Barr virus in various mammalian cells," *Nature*, 313:812-815, 1985.

Yu et al., "Induced pluripotent stem cell lines derived from human somatic cells," *Science*, 318: 1917-1920, 2007.

Yu et al., Supporting Online Material for: "Induced pluripotent stem cell lines derived from human somatic cells," *Science*, available at http://www.sciencemag.org/cgi/data/1151526/DC1/2, Nov. 20, 2007.

PCT International Preliminary Report on Patentability, issued in International application No. PCT/US2009/046209, dated Dec. 16, 2010.

Okita et al., "Generation of mouse induced pluripotent stem cells without viral vectors," *Science*, 322:949-953, 2008.

* cited by examiner

METHODS FOR THE PRODUCTION OF IPS CELLS USING NON-VIRAL APPROACH

This application claims priority to U.S. Application No. 61/058,858 filed on Jun. 4, 2008 and U.S. Application No. 61/160,584 filed on Mar. 16, 2009, the entire disclosures of which are specifically incorporated herein by reference in their entirety without disclaimer.

BACKGROUND OF THE INVENTION

1. Field of the Invention

The present invention relates generally to the field of molecular biology, stem cells and differentiated cells. More particularly, it concerns differentiation programming or reprogramming of somatic cells and undifferentiated cells.

2. Description of Related Art

In general, stem cells are undifferentiated cells which can give rise to a succession of mature functional cells. For example, a hematopoietic stem cell may give rise to any of the different types of terminally differentiated blood cells. Embryonic stem (ES) cells are derived from the embryo and are pluripotent, thus possessing the capability of developing into any organ or tissue type or, at least potentially, into a complete embryo.

Induced pluripotent stem cells, commonly abbreviated as iPS cells or iPSCs, are a type of pluripotent stem cell artificially derived from a non-pluripotent cell, typically an adult somatic cell, by inserting certain genes. Induced pluripotent stem cells are believed to be identical to natural pluripotent stem cells, such as embryonic stem cells in many respects, such as in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

IPS cells were first produced in 2006 (Takahashi et al., 2006) from mouse cells and in 2007 from human cells (Takahashi et al., 2007; Yu et al, 2007). This has been cited as an important advancement in stem cell research, as it may allow researchers to obtain pluripotent stem cells, which are important in research and potentially have therapeutic uses, without the controversial use of embryos.

However, at this stage in the study of these induced pluripotent stem (iPS) cells, researchers are using integrating viral plasmids, which insert the genes into the genome of target cells, potentially introducing mutations at the insertion site. Therefore, there is a need to develop a method to induce pluripotent stem cells essentially free of exogenous viral components.

Due to the significant medical potential of cell therapy and tissue transplantation, there also exists an urgent need for the production of any desired cell types by altering cellular differentiation status of an available cell population. Each specialized cell type in an organism expresses a subset of all the genes that constitute the genome of that species. Each cell type is defined by its particular pattern of regulated gene expression. Cell differentiation is thus a transition of a cell from one cell type to another and it involves a switch from one pattern of gene expression to another. Cellular differentiation during development can be understood as the result of a gene regulatory network. A regulatory gene and its cis-regulatory modules are nodes in a gene regulatory network; they receive input and create output elsewhere in the network. The similar mechanisms may also apply to dedifferentiation, for example, inducing pluripotency from somatic cells as mentioned above, and transdifferentiation, specifically referring to transformation of one differentiated cell type into another. Transcription factors controlling the development choices have been studied to change differentiation status; however, viral vectors have also been widely used. Therefore, there is a need for improved viral free differentiation programming methods.

SUMMARY OF THE INVENTION

The present invention overcomes a major deficiency in the art in providing induced pluripotent stem cells and other desired cell types essentially free of exogenous vector elements by differentiation programming. In a first embodiment there is provided a method for producing an induced pluripotent stem (iPS) cell population, the method comprising the steps of: a) obtaining a reprogramming vector, element of the vector comprising a replication origin and one or more expression cassettes encoding iPS reprogramming factors; b) introducing the reprogramming vector into cells of a population of somatic cells; c) culturing the cells to expand the population; d) selecting progeny cells of said expanded population, wherein said progeny has one or more characteristics of embryonic stem cells; and e) culturing the selected progeny cells to provide the iPS cell population, wherein one or more of said expression cassettes comprise a nucleotide sequence encoding a trans-acting factor that binds to the replication origin to replicate an extra-chromosomal template, and/or wherein the somatic cells express such a trans-acting factor. In a further aspect, step c or step e further comprises culturing until the cells are essentially free of the vector elements or comprise an additional selection step as described below to facilitate generation of vector-free iPS cells.

In certain aspects, in order to replicate an extra-chromosomal template, one or more of the expression cassettes comprise a nucleotide sequence encoding a trans-acting factor that binds to the replication origin; alternatively, the somatic cells comprise a nucleotide sequence encoding a trans-acting factor that binds to the replication origin.

In exemplary embodiments, the replication origin may be a replication origin of a lymphotrophic herpes virus or a gammaherpesvirus, an adenovirus, SV40, a bovine papilloma virus, or a yeast, such as a replication origin of a lymphotrophic herpes virus or a gammaherpesvirus corresponding to oriP of EBV. In a further aspect, the lymphotrophic herpes virus may be Epstein Barr virus (EBV), Kaposi's sarcoma herpes virus (KSHV), Herpes virus saimiri (HS), or Marek's disease virus (MDV). In a still further aspect, the gammaherpesvirus may be Epstein Barr virus (EBV) or Kaposi's sarcoma herpes virus (KSHV).

In certain embodiments, the trans-acting factor may be a polypeptide corresponding to, or a derivative, of a wild-type protein corresponding to EBNA-1 of EBV, preferably in the presence of a replication origin corresponding to OriP of EBV. The derivative may have a reduced ability to activate transcription from an integrated template as compared to wild-type EBNA-1 and thus reduced chances to ectopically activate chromosome genes to cause oncogenic transformation. Meanwhile, the derivative may activate transcription at least 5% that of the corresponding wild-type protein from an extra-chromosomal template after the derivative binds the replication origin. Such a derivative may have a deletion of residues corresponding to residues about 65 to about 89 of wild-type EBNA-1 (SEQ ID NO:1 referring to the wild-type EBNA-1 protein sequence, which is encoded by SEQ ID NO:2), and/or has a deletion of residues corresponding to residues about 90 to about 328 of EBNA-1 (SEQ ID NO:1), or may be a derivative with at least 80% amino acid sequence identity to residues 1 to about 40 and residues about 328 to 641 of EBNA-1 (SEQ ID NO:1). Amino acids 90-328 of wild-type EBNA-1 comprise a region rich in Gly-Ala repeats that should not contribute significantly to EBNA-1's function in the present invention and therefore this region may be variable in terms of the number of repeats present (i.e., the region may be deleted all or in part). An exemplary derivative of a wild-type EBNA-1 may have a sequence of SEQ ID NO:3, which is encoded by SEQ ID NO:4.

In certain further embodiments, the invention involves an additional step of selecting progeny cells of the expanded population, wherein the progeny is essentially free of the vector elements. Because extra-chromosomally replicated vectors, such as OriP-based vectors will be lost from cells over time, such as during two-week post-transfection and iPS cells does not need exogenous reprogramming factors after entering a self-maintaining pluripotent state, this optional additional selection step may help accelerate generation of vector-free pluripotent stem cells. Therefore, the additional step may be at a time after the progeny cells enter a self-sustaining pluripotent state, such as at least about 10 days to at least 30 days after the reprogramming vectors are introduced into cells. To facilitate the process to generate vector element-free iPS cells, the reprogramming vector may further comprise a nucleotide sequence encoding a negative selection marker, and the additional step selects progeny cells of the expanded population by eliminating progeny cells comprising the selection marker with a selection agent. For example, the selection marker may encode herpes simplex virus-thymidine kinase, allowing for application of a selection agent such as gancyclovir to remove cells with residual vectors encoding the kinase. In certain aspects, the iPS cell population generated by the methods is essentially free of the selection marker. An alternative or complementary approach is to test the absence of exogenous genetic elements in progeny cells, using conventional methods, such as RT-PCR, PCR, FISH (Fluorescent in situ hybridization), gene array, or hybridization (e.g., Southern blot).

In some embodiments, the iPS cell population generated from the above methods may be essentially free of integrated, reprogramming vector genetic elements, or essentially free of vector genetic elements.

In a further aspect, the reprogramming vector may be introduced into the cells by liposome transfection, electroporation, particle bombardment, calcium phosphate, polycation, or polyanion or any methods suitable for introducing exogenous genetics elements into the cells.

In still further aspects of the invention, the somatic cells may be from mammals, or more specifically, humans. The somatic cells may be terminally differentiated cells, or tissue stem cells, including, but not limited to, fibroblasts, hematopoietic cells, or mesenchymal cells. For example, the somatic cells are fibroblasts. The somatic cells may be from a tissue cell bank or from a selected human subject, specifically, a live human. Genomes from progeny of these somatic cells will be considered to be derived from these somatic cells of a certain source, such as a selected human individual.

In some further aspects, the progeny cells could be selected for one or more embryonic stem cell characteristics, such as an undifferentiated morphology, an embryonic stem cell-specific marker or pluripotency or multi-lineage differentiation potential or any characteristics known in the art. Specifically, the progeny cells may be selected for an undifferentiated morphology because of its convenience. The embryonic stem cell-specific marker could be one or more specific markers selected from the group consisting of SSEA-3, SSEA-4, Tra-1-60 or Tra-1-81, Tra-2-49/6E, GDF3, REX1, FGF4, ESG1, DPPA2, DPPA4, and hTERT. This selection step may be employed at more than one time points after transfection to ensure that cells are in a pluripotent state and does not return to a differentiated state.

Furthermore, in certain aspects of the invention, positive selection markers are known in the art and may be used in the methods and compositions of the invention to improved the efficiency of transfection or concentration of transfected cells in a time period sufficient for establishment of a self-sustaining pluripotent state. For example, in some aspects, the reprogramming vector may further comprise a positive selection marker such as a nucleotide sequence encoding a antibiotic resistance factor (e.g., neomycin or hygromycin resistance marker), or a fluorescent or luminescent protein (e.g., GFP, RFP, CFP, etc.). After the somatic cells are introduced with the reprogramming vector, use of the positive selection marker may help concentrate cells having reprogramming vectors. However this step is optional and depends on the transfection efficiency and vector loss rate. If transfection efficiency is high (such as more than 90%) and the vectors loss is sufficiently slow for cells to establish a self-sustaining pluripotent state, this positive selection may not be necessary.

In still further embodiments of the invention, the iPS reprogramming factors may comprise at least one member from Sox family and at least one member from Oct family, specifically, Sox-2 and Oct-4. Sox and Oct are thought to be central to the transcriptional regulatory hierarchy that specifies ES cell identity. Additional factors may increase the reprogramming efficiency, such as a set comprising Sox-2, Oct-4, Nanog and, optionally, Lin-28; or comprising Sox-2, Oct-4, Klf and, optionally, c-Myc.

In some further aspects of the above methods, step d may range from at least 8 days to at least 30 days, or any intermediating days of the preceding numbers after the step b, for the time period required to establish a self-sustaining pluripotent state.

The skilled artisan will understand that expression cassettes may be operably linked to a transcriptional regulator element, such as promoter or enhancer.

In a further aspect, a reprogramming vector, comprising a replication origin and one or more expression cassettes encoding a trans-acting factor that binds to the replication origin to replicate an extra-chromosomal template; and iPS reprogramming factors is also disclosed. The iPS reprogramming factors may comprise Sox and Oct, more specifically, Sox-2 and Oct-4, for example, a set which comprises Sox-2, Oct-4, Nanog and, optionally, Lin-28; or comprises Sox-2, Oct-4, Klf and, optionally, c-Myc.

In certain aspects of the reprogramming vector, wherein the reprogramming vector replicates extra-chromosomally and/or lacks the ability to be integrated into a host cell genome. In exemplary embodiments, the replication origin may be a replication origin of a lymphotrophic herpes virus or a gammaherpesvirus, an adenovirus, SV40, a bovine papilloma virus, or a yeast, such as a replication origin of a lymphotrophic herpes virus or a gammaherpesvirus corresponding to oriP of EBV. In a further aspect, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gammaherpesvirus.

In certain embodiments of the reprogramming vector, the trans-acting factor may be a polypeptide corresponding to, or a derivative of a wild-type protein corresponding to EBNA-1 of EBV. The derivative may activate transcription at least 5% that of the corresponding wild-type protein from an extra-chromosomal template after the derivative binds the replication origin, and/or have a reduced ability to activate transcription from an integrated template as compared to wild-type EBNA-1 and thus reduced chances to ectopically activate chromosome genes to cause oncogenic transformation.

Example of a derivative may include a derivative which lacks sequences present in the wild-type EBNA-1 protein that activate transcription from an integrated template, a derivative which has a nuclear localization sequence, a derivative which has a deletion of residues corresponding to residues about 65 to about 89 of EBNA-1 (SEQ ID NO:1), and/or has a deletion of residues corresponding to residues about 90 to about 328 of EBNA-1 (SEQ ID NO:1), a derivative with at least 80% amino acid sequence identity to residues 1 to about 40 and residues about 328 to 641 of EBNA-1 (SEQ ID NO:1), or a derivative comprising a first nucleotide sequence encoding residues 1 to about 40 of the corresponding wild-type EBNA-1 and a second nucleotide sequence encoding residues about 328 to 641 of the corresponding wild-type EBNA-1.

In a further aspect, an iPS cell population produced according to the preceding method is also claimed. In a still further aspect, there may be also disclosed an iPS cell population that is essentially free of exogenous retroviral elements or an iPS cell population essentially free of exogenous viral elements or any exogenous nucleic acid elements, such as vector genetic elements; more specifically, the cell population may comprise the genome of a selected human individual. In a further aspect, an iPS cell population may comprise cells whose genome is derived from a terminally differentiated human cell such as a primary skin cell (e.g., a fibroblast) and essentially free of exogenous retroviral elements or any exogenous nucleic acid or vector genetic elements. "Essentially free" of exogenous DNA elements means that less than 1%, 0.5%, 0.1%, 0.05% or any intermediate percentage of cells of iPS cell population comprises exogenous DNA elements.

In a still further aspect, a differentiated cell, tissue or organ, which has been differentiated from the iPS cell population as described above may be disclosed. The differentiated cell may comprise a hematopoietic cell, a myocyte, a neuron, a fibroblast or an epidermal cell; the tissue may comprise nerve, bone, gut, epithelium, muscle, cartilage or cardiac tissue; the organ may comprise brain, spinal cord, heart, liver, kidney, stomach, intestine or pancreas. In certain aspects, the differentiated cell, tissue or organ may be used in tissue transplantation, drug screen or developmental research to replace embryonic stem cells.

The viral-free methods can be used for inducing any changes in differentiation status of a cell. In certain aspects, there is also provided a method of providing a cell population having an altered differentiation status relative to a starting cell population and having cells that are essentially free of programming vector genetic elements, the method comprising the steps of: a) obtaining a starting population of cells having a first differentiation status; b) obtaining one or more differentiation programming vectors, each vector comprising a replication origin and one or more expression cassettes encoding one or more differentiation programming factors that, in combination, can alter the differentiation status of the starting cell population to a second differentiation status, wherein one or more of said expression cassettes comprise a nucleotide sequence encoding a trans-acting factor that binds to the replication origin to replicate an extra-chromosomal template, and/or wherein the cells of the starting population express such a trans-acting factor; c) introducing the differentiation programming vector(s) into cells of the starting cell population; d) culturing the cells to effect expression of the one or more reprogramming factors such that traits consistent with the second differentiation status arise in at least a portion of cultured cells; and e) further culturing cells having the traits for a sufficient number of generations to provide a cell population that comprise cells having the second differentiation status but which cells are essentially free of programming vector genetic elements.

In certain aspects, in order to replicate an extra-chromosomal template, one or more of the expression cassettes in at least a differentiation programming vector comprise a nucleotide sequence encoding a trans-acting factor that binds to the replication origin; alternatively, the starting cells may comprise a nucleotide sequence encoding a trans-acting factor that binds to the replication origin.

There may be three ways of altering the differentiation status in the present invention: dedifferentiation (which may be further defined as reprogramming), differentiation, or transdifferentiation.

In a certain aspect of the invention, an example of dedifferentiation is induction of pluripotency from somatic cells, such as a fibroblast, a keratinocyte, a hematopoietic cell (e.g., a lymphocyte), a mesenchymal cell, a liver cell, a stomach cell, or a β cell. The traits of the cells of the second differentiation status can be further defined as one or more characteristics of embryonic stem cells. To induce pluripotency in the differentiation programming methods, the programming factors may be further defined as reprogramming factors that comprise Sox and Oct, more specifically, Sox-2 and Oct-4, optionally in combination with one or more additional factors, such as Nanog, Lin-28, Klf, c-Myc or Esrrb. The starting cell may also be a less differentiated cell, such as a hematopoietic stem cell, a neural stem cell, or a mesenchymal stem cell, or corresponding progenitor cells, which may express certain programming factors endogenously and may be more easily reprogrammed into pluripotent cells with the need of less factors. For example, neural progenitor cells may be reprogrammed into pluripotent cells in the absence of exogenous Sox-2 expression. The method may also include an additional step of differentiating of the target cell population which is programmed to a more pluripotent status based on the steps described above.

In another aspect, differentiation methods are also included, such as inducing a more specified cell fate of a pluripotent or a multipotent cell: for example, differentiation of an embryonic stem cell or an induced pluripotent stem cell into a more differentiated cell, such as a hematopoietic progenitor, an endoderm progenitor, a pancreatic progenitor, an endothelial progenitor, or a retina progenitor, or even further to a terminally differentiated cell, such as a cardiomyocyte, a blood cell, a neuron, a hepatocyte, an islet beta cell, or a retina cell; or differentiation of a multipotent cell like a hematopoietic stem cell, a neural stem cell, or a mesenchymal stem cell as well as a hematopoietic progenitor, an endoderm progenitor, a pancreatic progenitor, or an endothelial progenitor. A specific example is that a pluripotent cell may be differentiated into an endoderm progenitor with the methods using SOX, such as SOX7 or SOX17, as the programming factors. Another example is that a hematopoietic progenitor may be differentiated into a B lymphocyte with the methods using EBF1 as the differentiation programming factor.

In a further aspect, the methods of the present invention can be also used for transdifferentiation of a differentiated cell type to another differentiated cell type. The starting cell and the altered cell may both be terminally or particularly differentiated, for example, a B lymphocyte may be programmed into a macrophage with programming factors such as C/EBP (more specifically, C/EBPα and C/EBPβ), or an exocrine cell may be programmed into a hepatocyte with factors such as C/EBPβ or into an islet β-cell with factors comprising Ngn3 (also known as Neurog3), Pdx1 and Mafa.

Furthermore, in certain aspects of the invention, the methods may also comprise an additional step of selecting cells of the cultured cells, which cells are essentially free of differentiation programming vector genetic elements, for example, by selecting cells of the cultured cells, which cells are essentially free of a selection marker comprised in the differentiation programming vector, or by directly testing the presence of vector genetic elements by methods known in the art. For example, the programming vector may comprise a selection marker such as a nucleotide sequence encoding a antibiotic resistance factor (e.g., neomycin or hygromycin resistance marker), a fluorescent or luminescent protein (e.g., GFP, RFP, CFP, etc.), or an enzyme (e.g., thymidine kinase). The selection for loss of vector genetic elements may be at or after a time when the second differentiation status has been established.

In a further aspect, the differentiation programming vector may be introduced into the starting cells by liposome transfection, electroporation, particle bombardment, calcium phosphate, polycation, or polyanion or any methods suitable for introducing exogenous genetics elements into the cells. The starting cells may be mammalian cells, more specifically, human cells. In a further aspect, a cell of the second differentiation status and essentially free of vector genetic elements produced according to the preceding methods is also provided.

In a still further aspect, there is also provided a differentiation programming vector, comprising a replication origin and one or more expression cassettes encoding a trans-acting factor that binds to the replication origin to replicate an extra-chromosomal template; and one or more differentiation programming factors. The differentiation programming factors may be selected from the group consisting of Sox (e.g., Sox-2, Sox-7, Sox-17), Oct (e.g., Oct-4), Nanog, Lin-28, Klf, c-Myc, Esrrb, EBF1, C/EBP (e.g., C/EBPα, C/EBPβ), Ngn3, Pdx and Mafa. Specific examples of the differentiation programming vector backbone may be an episomal expression vector, such as pCEP4, pREP4, or pEBNA DEST from Invitrogen. In a certain aspect, the differentiation programming vector may be further defined as reprogramming vector. The reprogramming vector may comprise a Sox family member and an Oct family member, such as Sox-2 and Oct-4, and may further comprise one or more factors, such as Nanog, Lin-28, Klf4, c-Myc, or Essrb.

In certain aspects of the differentiation programming vector, the replication origin may be a replication origin of a lymphotrophic herpes virus or a gamma herpesvirus, an adenovirus, SV40, a bovine papilloma virus, or a yeast, specifically a replication origin of a lymphotrophic herpes virus or a gamma herpesvirus corresponding to oriP of EBV. In a particular aspect, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus.

In further embodiments of the differentiation programming vector, the trans-acting factor may be a polypeptide corresponding to, or a derivative of a wild-type protein corresponding to EBNA-1 of EBV. The derivative may activate transcription at least 5% that of the corresponding wild-type protein from an extra-chromosomal template after the derivative binds the replication origin, and/or have a reduced ability to activate transcription from an integrated template as compared to wild-type EBNA-1 and thus reduced chances to ectopically activate chromosome genes to cause oncogenic transformation. Example of a derivative may include a derivative which lacks sequences present in the wild-type EBNA-1 protein that activate transcription from an integrated template, a derivative which has a nuclear localization sequence, a derivative which has a deletion of residues corresponding to residues about 65 to about 89 of EBNA-1, and/or has a deletion of residues corresponding to residues about 90 to about 328 of EBNA-1, a derivative with at least 80% amino acid sequence identity to residues 1 to about 40 and residues about 328 to 641 of EBNA-1, or a derivative comprising a first nucleotide sequence encoding residues 1 to about 40 of the corresponding wild-type EBNA-1 and a second nucleotide sequence encoding residues about 328 to 641 of the corresponding wild-type EBNA-1.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4: Examples of cassettes to be integrated into a recipient backbone plasmid. Examples of promoters that could be used for expression include, but are not limited to, PGK, CMV, SV40, and EF1a.

DESCRIPTION OF ILLUSTRATIVE EMBODIMENTS

I. The Present Invention

Figure 1:
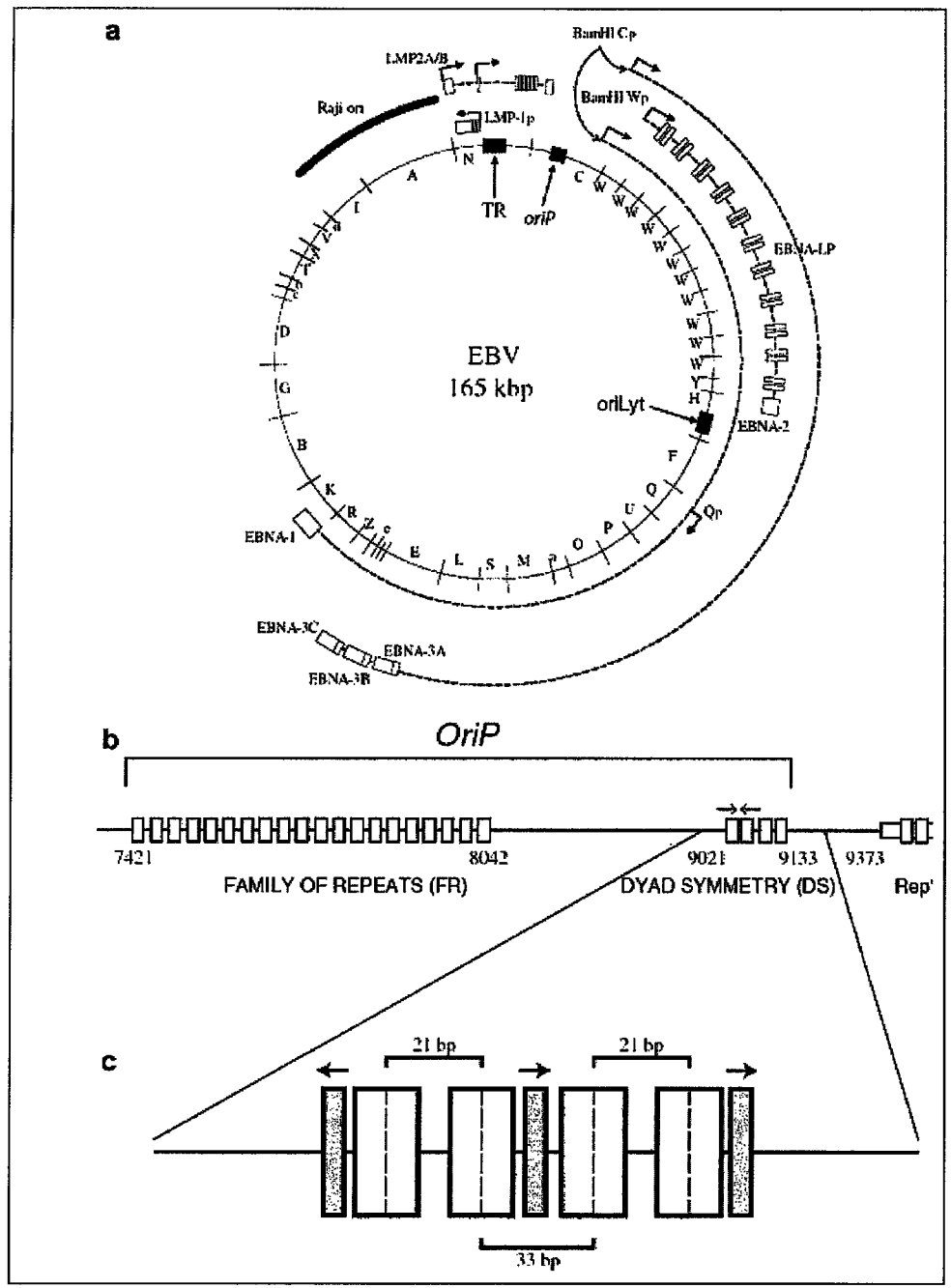
FIG. 1: The EBV genome and the latent origin of plasmid replication (oriP).

The instant invention overcomes several major problems with current reprogramming technologies or differentiation programming of various developmental stages of cells, such as generating induced pluripotent stem cells that are essentially free of viral vectors or exogenous elements. In contrast to previous methods using integrating viral vectors, these methods use extra-chromosomally reprogramming or differentiation programming vectors, for example, EBV element-based plasmids, to transduce reprogramming or differentiation programming factors into somatic cells or stem cells, culture these cells and select progeny cells for one or more embryonic stem cell characteristics or cells for traits consistent with an desired altered differentiation status. The extra-chromosomally replicated vectors, like EBV element-based vectors, will not be integrated into the host cell genome and will be lost over time after a period sufficient to induce cells into a pluripotent or a desired cell state. An inherent feature of these methods will produce progeny cells essentially free of exogenous genetic elements and a negative selection may facilitate the process. These methods enable isolation of iPS cells or any desired cell types essentially free of vector elements by altering differentiation status. Thus, the new compositions and methods will enable manufacture of vector-free iPS cells or other desired cell types for therapeutics without the risk of mutagenesis caused by random insertion or persistent expression of viral elements in the cells. Further embodiments and advantages of the invention are described below.

II. Definitions

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 1%, 5%, 25% or more in the in order of increasing preference.

"Differentiation programming" is a process that changes a cell to form progeny of at least one new cell type with a new differentiation status, either in culture or in vivo, than it would have under the same conditions without differentiation reprogramming. This process includes differentiation, dedifferentiation and transdifferentiation. "Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type.

An "origin of replication" ("ori") or "replication origin" is a DNA sequence, e.g., in a lymphotrophic herpes virus, that when present in a plasmid in a cell is capable of maintaining linked sequences in the plasmid, and/or a site at or near where DNA synthesis initiates. An ori for EBV includes FR sequences (20 imperfect copies of a 30 bp repeat), and preferably DS sequences, however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present invention may also use genetically engineered replication origin of EBV, such as by insertion or mutation of individual elements, as specifically described in Lindner, et. al., 2008.

A "lymphotrophic" herpes virus is a herpes virus that replicates in a lymphoblast (e.g., a human B lymphoblast) or other cell types and replicates extra-chromosomally for at least a part of its natural life-cycle. After infecting a host, these viruses latently infect the host by maintaining the viral genome as a plasmid. Herpes simplex virus (HSV) is not a "lymphotrophic" herpes virus. Exemplary lymphotropic herpes viruses include, but are not limited to EBV, Kaposi's sarcoma herpes virus (KSHV), Herpes virus saimiri (HS) and Marek's disease virus (MDV).

A "vector" or "construct" (sometimes referred to as gene delivery or gene transfer "vehicle") refers to a macromolecule or complex of molecules comprising a polynucleotide to be delivered to a host cell, either in vitro or in vivo.

A "plasmid", a common type of a vector, is an extra-chromosomal DNA molecule separate from the chromosomal DNA which is capable of replicating independently of the chromosomal DNA. In certain cases, it is circular and double-stranded.

A "template" as used herein is a DNA molecule which is specifically bound by a wild-type protein of a lymphotrophic herpes virus, which wild-type protein corresponds to EBNA-1, as a result of the presence in that template of a DNA sequence which is bound by the wild-type protein with an affinity that is at least 10% that of the binding of a DNA sequence corresponding to oriP of EBV by the wild-type protein and from which template transcription is optionally initiated and/or enhanced after the protein binds and/or the maintenance of which template in a cell is enhanced. An "integrated template" is one which is stably maintained in the genome of the cell, e.g., integrated into a chromosome of that cell. An "extra-chromosomal template" is one which is maintained stably maintained in a cell but which is not integrated into the chromosome.

By "expression construct" or "expression cassette" is meant a nucleic acid molecule that is capable of directing transcription. An expression construct includes, at the least, a promoter or a structure functionally equivalent to a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body which is a structural unit of tissue of a multicellular organism, is surrounded by a membrane structure which isolates it from the outside, has the capability of self replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self replication and pluripotency. Typically, stem cells can regenerate an injured tissue. Stem cells herein may be, but are not limited to, embryonic stem (ES) cells or tissue stem cells (also called tissue-specific stem cell, or somatic stem cell). Any artificially produced cell which can have the above-described abilities (e.g., fusion cells, reprogrammed cells, or the like used herein) may be a stem cell.

"Embryonic stem (ES) cells" are pluripotent stem cells derived from early embryos. An ES cell was first established in 1981, which has also been applied to production of knock-out mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by inserting certain genes, referred to as reprogramming factors.

"Pluripotency" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent cells or induced pluripotent cells.

As used herein "totipotent stem cells" refers to cells has the ability to differentiate into all cells constituting an organism, such as cells that are produced from the fusion of an egg and sperm cell. Cells produced by the first few divisions of the fertilized egg are also totipotent. These cells can differentiate into embryonic and extraembryonic cell types. Pluripotent stem cells can give rise to any fetal or adult cell type. However, alone they cannot develop into a fetal or adult animal because they lack the potential to contribute to extraembryonic tissue, such as the placenta.

In contrast, many progenitor cells are multipotent, i.e., they are capable of differentiating into a limited number of cell fates. Multipotent progenitor cells can give rise to several other cell types, but those types are limited in number. An example of a multipotent stem cell is a hematopoietic cell—a blood stem cell that can develop into several types of blood cells, but cannot develop into brain cells or other types of cells. At the end of the long series of cell divisions that form the embryo are cells that are terminally differentiated, or that are considered to be permanently committed to a specific function.

"Self-renewal" refers to the ability to go through numerous cycles of cell division while maintaining the undifferentiated state.

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

Cells are "substantially free" of exogenous genetic elements, as used herein, when they have less that 10% of the element(s), and are "essentially free" of exogenous genetic elements when they have less than 1% of the element(s). However, even more desirable are cell populations wherein less than 0.5% or less than 0.1% of the total cell population comprise exogenous genetic elements. Thus, iPS cell populations wherein less than 0.1% to 10% (including all intermediate percentages) of the cells of the population comprises undesirable exogenous genetic elements.

III. General Background for Induced Pluripotent Stem Cells

In certain embodiments of the invention, there are disclosed methods of reprogramming somatic cells by introducing reprogramming factors into somatic cells with an extrachromosomal vector-based system. The progeny of these cells could be identical to embryonic stem cells in various aspects as described below, but essentially free of exogenous genetic elements. Understanding of embryonic stem cell characteristics could help select induced pluripotent stem cells. Reprogramming factors known from stem cell reprogramming studies could be used for these novel methods. It is further contemplated that these induced pluripotent stem cells could be potentially used to replace embryonic stem cells for therapeutics and research applications due to the ethics hurdle to use the latter.

A. Stem Cells

Stem cells are cells found in most, if not all, multi-cellular organisms. They are characterized by the ability to renew themselves through mitotic cell division and differentiating into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues.

As stem cells can be grown and transformed into specialized cells with characteristics consistent with cells of various tissues such as muscles or nerves through cell culture, their use in medical therapies has been proposed. In particular, embryonic cell lines, autologous embryonic stem cells generated through therapeutic cloning, and highly plastic adult stem cells from the umbilical cord blood or bone marrow are touted as promising candidates. Most recently, the reprogramming of adult cells into induced pluripotent stem cells has enormous potential for replacing embryonic stem cells.

B. Embryonic Stem Cells

Embryonic stem cell lines (ES cell lines) are cultures of cells derived from the epiblast tissue of the inner cell mass (ICM) of a blastocyst or earlier morula stage embryos. A blastocyst is an early stage embryo—approximately four to five days old in humans and consisting of 50-150 cells. ES cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may be also defined by the presence of several transcription factors and cell surface proteins. The transcription factors Oct-4, Nanog, and Sox-2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

After twenty years of research, there are no approved treatments or human trials using embryonic stem cells. ES cells, being pluripotent cells, require specific signals for correct differentiation—if injected directly into the body, ES cells will differentiate into many different types of cells, causing a teratoma. Differentiating ES cells into usable cells while avoiding transplant rejection are just a few of the hurdles that embryonic stem cell researchers still face. Many nations currently have moratoria on either ES cell research or the production of new ES cell lines. Because of their combined abilities of unlimited expansion and pluripotency, embryonic stem cells remain a theoretically potential source for regenerative medicine and tissue replacement after injury or disease. However, one way to circumvent these issues is to induce pluripotent status in somatic cells by direct reprogramming.

C. Reprogramming Factors

The generation of iPS cells is crucial on the genes used for the induction. The following factors or combination thereof could be used in the vector system disclosed in the present invention. In certain aspects, nucleic acids encoding Sox and Oct (preferably Oct3/4) will be included into the reprogramming vector. For example, a reprogramming vector may comprise expression cassettes encoding Sox-2, Oct-4, Nanog and optionally Lin-28, or expression cassettes encoding Sox-2, Oct-4, Klf4 and optionally c-myc, or expression cassettes encoding Sox-2, Oct-4, and optionally Esrrb. Nucleic acids encoding these reprogramming factors may be comprised in the same expression cassette, different expression cassettes, the same reprogramming vector, or different reprogramming vectors.

Oct-3/4 and certain members of the Sox gene family (Sox-1, Sox-2, Sox-3, and Sox-15) have been identified as crucial transcriptional regulators involved in the induction process whose absence makes induction impossible. Additional genes, however, including certain members of the Klf family (Klf-1, Klf2, Klf4, and Klf5), the Myc family (C-myc, L-myc, and N-myc), Nanog, and LIN28, have been identified to increase the induction efficiency.

Oct-3/4 (Pou5f1) is one of the family of octamer ("Oct") transcription factors, and plays a crucial role in maintaining pluripotency. The absence of Oct-3/4 in Oct-3/4+ cells, such as blastomeres and embryonic stem cells, leads to spontaneous trophoblast differentiation, and presence of Oct-3/4 thus gives rise to the pluripotency and differentiation potential of embryonic stem cells. Various other genes in the "Oct" family, including Oct-3/4's close relatives, Oct1 and Oct6, fail to elicit induction, thus demonstrating the exclusiveness of Oct-3/4 to the induction process.

The Sox family of genes is associated with maintaining pluripotency similar to Oct-3/4, although it is associated with multipotent and unipotent stem cells in contrast with Oct-3/4, which is exclusively expressed in pluripotent stem cells. While Sox-2 was the initial gene used for induction by Yamanaka et al., Jaenisch et al., and Thompson et al., other genes in the Sox family have been found to work as well in the induction process. Sox1 yields iPS cells with a similar efficiency as Sox-2, and genes Sox3, Sox15, and Sox18 also generate iPS cells, although with decreased efficiency.

In embryonic stem cells, Nanog, along with Oct-3/4 and Sox-2, is necessary in promoting pluripotency. Therefore, it was surprising when Yamanaka et al. reported that Nanog was unnecessary for induction although Thomson et al. has reported it is possible to generate iPS cells with Nanog as one of the factors.

LIN28 is an mRNA binding protein expressed in embryonic stem cells and embryonic carcinoma cells associated with differentiation and proliferation. Thomson et al. demonstrated it is a factor in iPS generation, although it is unnecessary.

Klf4 of the Klf family of genes was initially identified by Yamanaka et al. and confirmed by Jaenisch et al. as a factor for the generation of mouse iPS cells and was demonstrated by Yamanaka et al. as a factor for generation of human iPS cells. However, Thompson et al. reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Yamanaka et al. and Jaenisch et al. demonstrated that c-myc is a factor implicated in the generation of mouse iPS cells and Yamanaka et al. demonstrated it was a factor implicated in the generation of human iPS cells. However, Thomson et al. and Yamanaka et al. reported that c-myc was unnecessary for generation of human iPS cells. Usage of the "myc" family of genes in induction of iPS cells is troubling for the eventuality of iPS cells as clinical therapies, as 25% of mice transplanted with c-myc-induced iPS cells developed lethal teratomas. N-myc and L-myc have been identified to induce in the stead of c-myc with similar efficiency.

D. Induction of Pluripotent Stem Cells Using Integrating Vectors

IPS cells are typically derived by transfection of certain stem cell-associated genes into non-pluripotent cells, such as adult fibroblasts. Transfection is typically achieved through integrating viral vectors in the current practice, such as retroviruses. Transfected genes include the master transcriptional regulators Oct-3/4 (Pouf51) and Sox-2, although it is suggested that other genes enhance the efficiency of induction. After a critical period, small numbers of transfected cells begin to become morphologically and biochemically similar to pluripotent stem cells, and are typically isolated through morphological selection, doubling time, or through a reporter gene and antibiotic infection.

In November 2007, a milestone was achieved by creating iPS from adult human cells from two independent research teams' studies (Yu et al., 2007; Yamanaka et al., 2007). With the same principle used earlier in mouse models, Yamanaka had successfully transformed human fibroblasts into pluripotent stem cells using the same four pivotal genes: Oct3/4, Sox-2, Klf4, and c-Myc with a retroviral system but c-Myc is oncogenic. Thomson and colleagues used Oct-4, Sox-2, NANOG, and a different gene LIN28 using a lentiviral system avoiding the use of c-Myc.

However, the viral transfection systems used insert the genes at random locations in the host's genome; this is a concern for potential therapeutic applications of these iPSCs, because the created cells might be susceptible to cancer. Members of both teams consider it therefore necessary to develop new delivery methods.

On the other hand, forced persistent expression of ectopic reprogramming factors may be linked to an elevated frequency of tumor formation and the final solution to this problem will be the generation of transgene-free iPS cells. A suite of virally introduced genes may be necessary to start the reprogramming process, but gradually the cell's own endogenous pluripotency genes become active, and the viral genes will be silenced with a potential to stochastic reactivated. Recently researchers demonstrate exogenous factors may be required for a minimum of about 10-16 days in order for cells to enter a self-sustaining pluripotent state (Brambrink et al., 2008; Stadtfeld et al., 2008). The determination of the minimum length of transgene expression permit the development of non-retroviral delivery methods to derive iPS cells, an advantage achieved by the present disclosed methods and iPS cells as described below.

IV. Extra-Chromosomal Vectors for Generating Vector-Free Induced Pluripotent Stem Cells and Other Cell Types As described above, induction of pluripotent stem cells from human somatic cells has been achieved using retroviruses or lentiviral vectors for ectopic expression of reprogramming genes. Recombinant retroviruses such as the Moloney murine leukemia virus have the ability to integrate into the host genome in a stable fashion. They contain a reverse transcriptase which allows integration into the host genome. Lentiviruses are a subclass of Retroviruses. They are widely adapted as vectors thanks to their ability to integrate into the genome of non-dividing as well as dividing cells. These viral vectors also have been widely used in a broader context: differentiation programming of cells, including dedifferentiation, differentiation, and transdifferentiation. The viral genome in the form of RNA is reverse-transcribed when the virus enters the cell to produce DNA, which is then inserted into the genome at a random position by the viral integrase enzyme. Therefore, current technology of successful reprogramming is dependent on integration-based viral approaches.

However, with the present technology, targeted integration is still no routine (Bode et al., 2000b) and the conventional alternative, random integration, may lead to insertional mutagenesis with unpredictable consequences in induced pluripotent stem cells. For the same reasons expression of the transgene can not be controlled since it is dependent on the chromatin context of the integration site (Baer et al., 2000). High level expression can only be achieved at favorable genomic loci but the danger exists that integration into highly expressed sites interferes with vital cellular functions of induced pluripotent stem cells.

In addition, there is increasing evidence for the existence of cellular defense mechanisms against foreign DNA which operate by down-regulating transgenes in a process that is accompanied by DNA methylation (Bingham, 1997, Garrick et al., 1998). Furthermore, viral components may act along with other factors to transform cells. Accompanied by the continual expression from a number of viral genes, the persistence of at least part of the viral genome within the cell may cause cell transformation. These genes may interfere with a cell's signaling pathway causing the observed phenotypic changes of the cell, leading to a transformed cell showing increased cell division, which is favorable to the virus.

Therefore, in certain embodiments, the present invention develops methods to generate induced pluripotent stem cells and other desired cell types essentially free of exogenous genetic elements, such as from retroviral or lentiviral vector used in the previous methods. These methods make use of extra-chromosomally replicating vectors, or vectors capable of replicating episomally. A number of DNA viruses, such as adenoviruses, Simian vacuolating virus 40 (SV40) or bovine papilloma virus (BPV), or budding yeast ARS (Autonomously Replicating Sequences)-containing plasmids replicate extra-chromosomally or episomally in mammalian cells. These episomal plasmids are intrinsically free from all these disadvantages (Bode et al., 2001) associated with integrating vectors but have never been publicly disclosed for generating induced pluripotent stem cells. A lymphotrophic herpes virus-based including or Epstein Barr Virus (EBV) as defined above may also replicate extra-chromosomally and help deliver reprogramming genes to somatic cells. Although the replication origins of these viruses or ARS element are well characterized, they have never been known for reprogramming differentiated cells to public until this disclosure.

For example, the plasmid-based approach used in the invention extracts robust elements necessary for the successful replication and maintenance of an EBV element-based system without compromising the system's tractability in a clinical setting as described in detail below. The essential EBV elements are OriP and EBNA-1 or their variants or functional equivalents. An additional advantage of this system is that these exogenous elements will be lost with time after being introduced into cells, leading to self-sustained iPS cells essentially free of these elements.

A. Epstein-Barr Virus

The Epstein-Barr Virus (EBV), also called Human herpesvirus 4 (HHV-4), is a virus of the herpes family (which includes Herpes simplex virus and Cytomegalovirus), and is one of the most common viruses in humans. EBV maintains its genome extra-chromosomally and works in collaboration with host cell machinery for efficient replication and maintenance (Lindner and Sugden, 2007), relying solely on two essential features for its replication and its retention within cells during cell division (Yates et al. 1985; Yates et al. 1984). One element, commonly referred to as oriP, exists in cis and serves as the origin of replication. The other factor, EBNA1, functions in trans by binding to sequences within oriP to promote replication and maintenance of the plasmid DNA. As a non-limiting example, the inventors extract these two features and use them in the context of a plasmid to shuttle the genes necessary for reprogramming somatic cells to facilitate the replication and sustained expression of these genes over conventional plasmids.

B. OriP

OriP is the site at or near which DNA replication initiates and is composed of two cis-acting sequences approximately 1 kilobase pair apart known as the family of repeats (FR) and the dyad symmetry (DS).

FR is composed of 21 imperfect copies of a 30 bp repeat and contains 20 high affinity EBNA1-binding sites (FIG. 1). When FR is bound by EBNA1, it both serves as a transcriptional enhancer of promoters in cis up to 10 kb away (Reisman and Sugden, 1986; Yates, 1988; Sugden and Warren, 1989; Wysokenski and Yates, 1989; Gahn and Sugden, 1995; Kennedy and Sugden, 2003; Altmann et al., 2006), and contributes to the nuclear retention and faithful maintenance of FR containing plasmids (Langle-Rouault et al., 1998; Kirchmaier and Sugden, 1995; Wang et al., 2006; Nanbo and Sugden, 2007). The efficient partitioning of oriP plasmids is also likely attributable to FR. While the virus has evolved to maintain 20 EBNA1-binding sites in FR, efficient plasmid maintenance requires only seven of these sites, and can be reconstituted by a polymer of three copies of DS, having a total of 12 EBNA1-binding sites (Wysokenski and Yates, 1989).

The dyad symmetry element (DS) is sufficient for initiation of DNA synthesis in the presence of EBNA1 (Aiyar et al., 1998; Yates et al., 2000), and initiation occurs either at or near DS (Gahn and Schildkraut, 1989; Niller et al., 1995). Termination of viral DNA synthesis is thought to occur at FR, because when FR is bound by EBNA1 it functions as a replication fork barrier as observed by 2D gel electrophoresis (Gahn and Schildkraut, 1989; Ermakova et al., 1996; Wang et al., 2006). Initiation of DNA synthesis from DS is licensed to once-per-cell-cycle (Adams, 1987; Yates and Guan, 1991), and is regulated by the components of the cellular replication system (Chaudhuri et al., 2001; Ritzi et al., 2003; Dhar et al., 2001; Schepers et al., 2001; Zhou et al., 2005; Julien et al., 2004). DS contains four EBNA1-binding sites, albeit with lower affinity than those found in FR (Reisman et al., 1985). The topology of DS is such that the four binding sites are arranged as two pairs of sites, with 21 bp center-to-center spacing between each pair and 33 bp center-to-center spacing between the two non-paired internal binding sites (FIG. 1c) (Baer et al., 1984; Rawlins et al., 1985).

The functional roles of the elements within DS have been confirmed by studies of another region of EBV's genome, termed Rep*, which was identified as an element that can substitute for DS inefficiently (Kirchmaier and Sugden, 1998). Polymerizing Rep* eight times yielded an element as efficient as DS in its support of replication (Wang et al., 2006). Biochemical dissection of Rep* identified a pair of EBNA 1-binding sites with a 21 bp center-to-center spacing critical for its replicative function (ibid). The minimal replicator of Rep* was found to be the pair of EBNA1-binding sites, as replicative function was retained even after all flanking sequences in the polymer were replaced with sequences derived from lambda phage. Comparisons of DS and Rep* have revealed a common mechanism: these replicators support the initiation of DNA synthesis by recruiting the cellular replicative machinery via a pair of appropriately spaced sites, bent and bound by EBNA1.

There are other extra-chromosomal, licensed plasmids that replicate in mammalian cells that are unrelated to EBV and in some ways appear similar to the zone of initiation within the Raji strain of EBV. Hans Lipps and his colleagues have developed and studied plasmids that contain "nuclear scaffold/matrix attachment regions" (S/MARs) and a robust transcriptional unit (Piechaczek et al., 1999; Jenke et al., 2004). Their S/MAR is derived from the human interferon-beta gene, is A/T rich, and operationally defined by its association with the nuclear matrix and its preferential unwinding at low ionic strength or when embedded in supercoiled DNA (Bode et al., 1992). These plasmids replicate semiconservatively, bind ORC proteins, and support the initiation of DNA synthesis effectively randomly throughout their DNA (Schaarschmidt et al., 2004). They are efficiently maintained in proliferating hamster and human cells without drug selection and when introduced into swine embryos can support expression of GFP in most tissues of fetal animals (Manzini et al., 2006).

C. EBNA1

Epstein Barr nuclear antigen 1 (EBNA1) is a DNA-binding protein that binds to FR and DS of oriP or Rep* to facilitate replication and faithful partitioning of the EBV plasmid to daughter cells independent of, but in concert with, cell chromosomes during each cell division.

Figure 2:
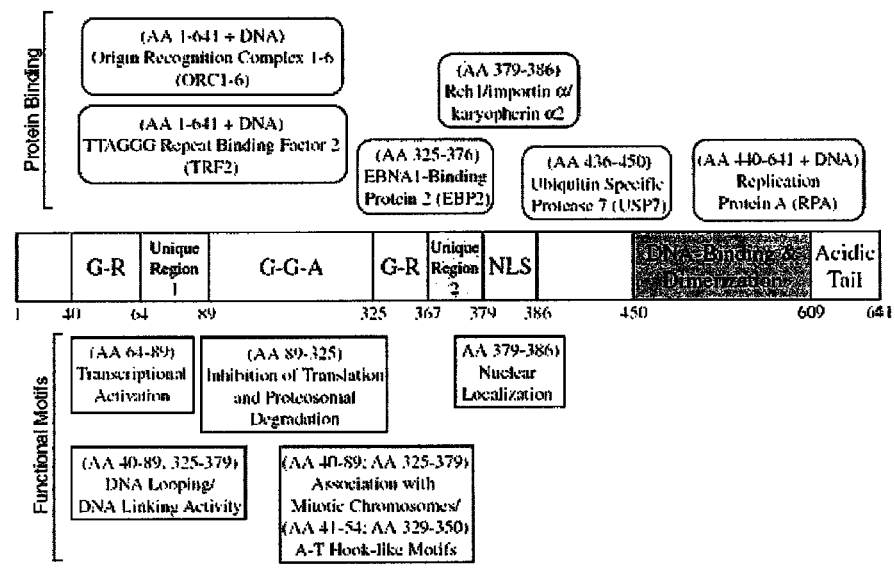
FIG. 2: A domain-based model and partial structure representation of EBNA1

The 641 amino acids (AA) of EBNA1 have been categorized into domains associated with its varied functions by mutational and deletional analyses (FIG. 2). Two regions, between AA40-89 and AA329-378 are capable of linking two DNA elements in cis or in trans when bound by EBNA1, and have thus been termed Linking Region 1 and 2 (LR1, LR2) (Middleton and Sugden, 1992; Frappier and O'Donnell, 1991; Su et al., 1991; Mackey et al., 1995). Fusing these domains of EBNA1 to GFP homes the GFP to mitotic chromosomes (Marechal et al., 1999; Kanda et al., 2001). LR1 and LR2 are functionally redundant for replication; a deletion of either one yields a derivative of EBNA1 capable of supporting DNA replication (Mackey and Sugden, 1999; Sears et al., 2004). LR1 and LR2 are rich in arginine and glycine residues, and resemble the AT-hook motifs that bind A/T rich DNA (Aravind and Landsman, 1998), (Sears et al., 2004). An in vitro analysis of LR1 and LR2 of EBNA1 has demonstrated their ability to bind to A/T rich DNA (Sears et al., 2004). When LR1, containing one such AT-hook, was fused to the DNA-binding and dimerization domain of EBNA1, it was found to be sufficient for DNA replication of oriP plasmids, albeit less efficiently than the wild-type EBNA1 (ibid).

LR1 and LR2 do differ, though. The C-terminal half of LR1 is composed of amino acids other than the repeated Arg-Gly of the N-terminal half, and is termed unique region 1 (UR1). UR1 is necessary for EBNA1 to activate transcription efficiently from transfected and integrated reporter DNAs containing FR (Wu et al., 2002; Kennedy and Sugden, 2003; Altmann et al., 2006). UR1 is also essential for the efficient transformation of B-cells infected by EBV. When a derivative of EBNA1 lacking this domain replaces the wild-type protein in the context of the whole virus, these derivative viruses have 0.1% of the transforming ability of the wild-type virus (Altmann et al., 2006).

LR2 is not required for EBNA1's support of oriP replication (Shire et al., 1999; Mackey and Sugden, 1999; Sears et al., 2004). Additionally, the N-terminal half of EBNA1 can be replaced with cellular proteins containing AT-hook motifs, such as HMGA1a, and still retain replicative function (Hung et al., 2001; Sears et al., 2003; Altmann et al., 2006). These findings indicate that it likely is the AT-hook activities of LR1 and LR2 are required for the maintenance of oriP in human cells.

A third of EBNA1's residues (AA91-328) consist of glycine-glycine-alanine (GGA) repeats, implicated in EBNA1's ability to evade the host immune response by inhibiting proteosomal degradation and presentation (Levitskaya et al., 1995; Levitskaya et al., 1997). These repeats have also been found to inhibit translation of EBNA1 in vitro and in vivo (Yin et al., 2003). However, the deletion of much of this domain has no apparent effect on functions of EBNA1 in cell culture, making the role that this domain plays difficult to elucidate.

A nuclear localization signal (NLS) is encoded by AA379-386, which also associates with the cellular nuclear importation machinery (Kim et al., 1997; Fischer et al., 1997). Sequences within the Arg-Gly rich regions of LR1 and LR2 may also function as NLSs due to their highly basic content.

Lastly, the C-terminus (AA458-607) encodes the overlapping DNA-binding and dimerization domains of EBNA1. The structure of these domains bound to DNA has been solved by X-ray crystallography, and was found to be similar to the DNA-binding domain of the E2 protein of papillomaviruses (Hegde et al., 1992; Kim et al., 2000; Bochkarev et al., 1996).

In specific embodiments of the invention, a reprogramming vector will contain both oriP and an abbreviated sequence encoding a version of EBNA1 competent to support plasmid replication and its proper maintenance during cell division. The highly repetitive sequence within the amino-terminal one-third of wild-type EBNA1 and removal of a 25 amino-acid region that has demonstrated toxicity in various cells are dispensable for EBNA1's trans-acting function associated with oriP (Yates et al. 1985; Kennedy et al. 2003). Therefore, an exemplary derivative, the abbreviated form of EBNA1, known as deltaUR1 (the derivative with a protein sequence SEQ ID NO:3, which is encoded by SEQ ID NO:4), could be used alongside oriP within this plasmid-based system. More examples of EBNA1 derivatives that can activate transcription from an extra-chromosomal template (see, for example, Kirchmaier and Sugden, 1997, and Kennedy and Sugden, 2003, both incorporated herein by reference.)

A derivative of EBNA-1 used in the invention is a polypeptide which, relative to a corresponding wild-type polypeptide, has a modified amino acid sequence. The modifications include the deletion, insertion or substitution of at least one amino acid residue in a region corresponding to the unique region (residues about 65 to about 89) of LR1 (residues about 40 to about 89) in EBNA-1, and may include a deletion, insertion and/or substitution of one or more amino acid residues in regions corresponding to other residues of EBNA-1, e.g., about residue 1 to about residue 40, residues about 90 to about 328 ("Gly-Gly-Ala" repeat region), residues about 329 to about 377 (LR2), residues about 379 to about 386 (NLS), residues about 451 to about 608 (DNA binding and dimerization), or residues about 609 to about 641, so long as the resulting derivative has the desired properties, e.g., dimerizes and binds DNA containing an ori corresponding to oriP, localizes to the nucleus, is not cytotoxic, and activates transcription from an extrachromosomal but does not substantially active transcription from an integrated template. Substitutions include substitutions which utilize the D rather than L form, as well as other well known amino acid analogs, e.g., unnatural amino acids such as α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α.-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, .omega.-N-methylarginine, and other similar amino acids and imino acids and tert-butylglycine.

Conservative amino acid substitutions are preferred—that is, for example, aspartic-glutamic as polar acidic amino acids; lysine/arginine/histidine as polar basic amino acids; leucine/isoleucine/methionine/valine/alanine/glycine/proline as nonpolar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

The invention also envisions polypeptides with non-conservative substitutions. Non-conservative substitutions entail exchanging a member of one of the classes described above for another.

Acid addition salts of the polypeptide or of amino residues of the polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

Analogs include structures having one or more peptide linkages optionally replaced by a linkage selected from the group consisting of: —$CH_2NH$—, —$CH_2S$—, —$CH_2$—$CH_2$—, —CH=CH-(cis and trans), —CH=CF-trans), —COCH2-, —CH(OH)$CH_2$—, and —$CH_2SO$—, by methods known in the art and further described in the following references: Spatola, 1983; Spatola, 1983; Morley, 1980; Hudson et al., 1979 (—$CH_2NH$—, $CH_2CH_2$—); Spatola et al., 1986 (—$CH_2$—S); Hann, 1982 (—CH—CH—, cis and trans); Almquist et al., 1980 (—$COCH_2$—); Jennings-White et al., 1982 (—$COCH_2$—); Szelke et al. European Appln. EP 45665 (—CH(OH)$CH_2$—); Holladay et al., 1983 (—C(OH)$CH_2$—); and Hruby, 1982 (—$CH_2S$—); each of which is incorporated herein by reference. A particularly preferred non-peptide linkage is —$CH_2NH$—. Such analogs may have greater chemical stability, enhanced pharmacological properties (half-life, absorption, potency, efficacy, etc.), altered specificity (e.g., a broad-spectrum of biological activities), reduced antigenicity, and be economically prepared.

D. Residue-Free Feature

Importantly, the replication and maintenance of oriP-based plasmids is imperfect and is lost precipitously (25% per cell division) from cells within the first two weeks of its being introduced into cells; however, those cells that retain the plasmid lose it less frequently (3% per cell division) (Leight and Sugden, 2001; Nanbo and Sugden, 2007). Once selection for cells harboring the plasmid is removed, plasmids will be lost during each cell division until all of them have been eliminated over time without leaving a footprint of its former existence within the resulting daughter cells. It is this footprintless feature that underlies the appeal of the oriP-based system as an alternative to the current viral-associated approach to deliver genes to generate iPS cells and other desired cells with differentiation programming. Other extra-chromosomal vectors will also be lost during replication and propagation of host cells and could also be employed in the present invention.

V. Vector Construction and Delivery

In certain embodiments, reprogramming or differentiation programming vectors could be constructed to comprise additional elements in addition to nucleic acid sequences encoding reprogramming factors or differentiation programming factors as described above to express these reprogramming factors in cells. The novel features of these methods are use of extra-chromosomally replicating vectors, which will not be integrated into the host cell genome and may be lost during generations of replication. Details of components of these vectors and delivery methods are disclosed below.

A. Vector

The use of plasmid- or liposome-based extra-chromosomal vectors, e.g., oriP-based vectors, and/or vectors encoding a derivative of EBNA-1 permit large fragments of DNA to be introduced to a cell and maintained extra-chromosomally, replicated once per cell cycle, partitioned to daughter cells efficiently, and elicit substantially no immune response. In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also other sources of episome-base vectors are contemplated, such as yeast ARS, adenovirus, SV40, or BPV.

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

B. Regulatory Elements:

Eukaryotic expression cassettes included in the vectors preferably contain (in a 5'-to-3' direction) a eukaryotic transcriptional promoter operably linked to a protein-coding sequence, splice signals including intervening sequences, and a transcriptional termination/polyadenylation sequence.

i. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

Promoters suitable for use in EBNA-1-encoding vector of the invention are those that direct the expression of the expression cassettes encoding the EBNA-1 protein to result in sufficient steady-state levels of EBNA-1 protein to stably maintain EBV oriP-containing vectors. Promoters are also used for efficient expression of expression cassettes encoding reprogramming factors.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, S.Y., Nuc. Acid Res. 17: 601-615, 1989, Quitsche et al., J. Biol. Chem. 264: 9539-9545, 1989), GADPH promoter (Alexander et al., Proc. Nat. Acad. Sci. USA 85: 5092-5096, 1988, Ercolani et al., J. Biol. Chem. 263: 15335-15341, 1988), metallothionein promoter (Karin et al. Cell 36: 371-379, 1989; Richards et al., Cell 37: 263-272, 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

ii. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

iii. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

iv. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

v. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

vi. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

vii. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in differentiation programming, which is a specific nucleic acid sequence at which replication is initiated. Alternatively a replication origin of other extra-chromosomally replicating virus as described above or an autonomously replicating sequence (ARS) can be employed.

viii. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art. One feature of the present invention includes using selection and screenable markers to select vector-free cells after the differentiation programming factors have effected a desired altered differentiation status in those cells.

C. Vector Delivery

Introduction of a reprogramming or differentiation programming vector into somatic cells with the current invention may use any suitable methods for nucleic acid delivery for transformation of a cell., as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al, 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952, 500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

i. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen). The amount of liposomes used may vary upon the nature of the liposome as well as the, cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

ii. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

iii. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

iv. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

v. Sonication Loading

Additional embodiments of the present invention include the introduction of a nucleic acid by direct sonic loading. LTK⁻ fibroblasts have been transfected with the thymidine kinase gene by sonication loading (Fechheimer et al., 1987).

vi. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

vii Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

VI. Selection of iPS Cells

In certain aspects of the invention, after a reprogramming vector is introduced into somatic cells, cells will be cultured for expansion (optionally selected for the presence of vector elements like positive selection or screenable marker to concentrate transfected cells) and reprogramming vectors will express reprogramming factors in these cells and replicate and partition along with cell division. These expressed reprogramming factors will reprogram somatic cell genome to establish a self-sustaining pluripotent state, and in the meantime or after removal of positive selection of the presence of vectors, exogenous genetic elements will be lost gradually. These induced pluripotent stem cells could be selected from progeny derived from these somatic cells based on embryonic stem cell characteristics because they are expected to be substantially identical to pluripotent embryonic stem cells. An additional negative selection step could be also employed to accelerate or help selection of iPS cells essentially free of exogenous genetic elements by testing the absence of reprogramming vector DNA or using selection markers.

A. Selection for Embryonic Stem Cell Characteristics

The successfully generated iPSCs from previous studies were remarkably similar to naturally-isolated pluripotent stem cells (such as mouse and human embryonic stem cells, mESCs and hESCs, respectively) in the following respects, thus confirming the identity, authenticity, and pluripotency of iPSCs to naturally-isolated pluripotent stem cells. Thus, induced pluripotent stem cells generated from the methods disclosed in this invention could be selected based on one or more of following embryonic stem cell characteristics.

i. Cellular Biological Properties

Morphology: iPSCs are morphologically similar to ESCs. Each cell may have round shape, large nucleolus and scant cytoplasm. Colonies of iPSCs could be also similar to that of ESCs. Human iPSCs form sharp-edged, flat, tightly-packed colonies similar to hESCs and mouse iPSCs form the colonies similar to mESCs, less flatter and more aggregated colonies than that of hESCs.

Growth properties: Doubling time and mitotic activity are cornerstones of ESCs, as stem cells must self-renew as part of their definition. iPSCs could be mitotically active, actively self-renewing, proliferating, and dividing at a rate equal to ESCs.

Stem Cell Markers: iPSCs may express cell surface antigenic markers expressed on ESCs. Human iPSCs expressed the markers specific to hESC, including, but not limited to, SSEA-3, SSEA-4, TRA-1-60, TRA-1-81, TRA-2-49/6E, and Nanog. Mouse iPSCs expressed SSEA-1 but not SSEA-3 nor SSEA-4, similarly to mESCs.

Stem Cell Genes: iPSCs may express genes expressed in undifferentiated ESCs, including Oct-3/4, Sox-2, Nanog, GDF3, REX1, FGF4, ESG1, DPPA2, DPPA4, and hTERT.

Telomerase Activity: Telomerases are necessary to sustain cell division unrestricted by the Hayflick limit of ~50 cell divisions. hESCs express high telomerase activity to sustain self-renewal and proliferation, and iPSCs also demonstrate high telomerase activity and express hTERT (human telomerase reverse transcriptase), a necessary component in the telomerase protein complex.

Pluripotency: iPSCs will be capable of differentiation in a fashion similar to ESCs into fully differentiated tissues.

Neural Differentiation: iPSCs could be differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes will be downregulated after differentiation.

Cardiac Differentiation: iPSCs could be differentiated into cardiomyocytes that spontaneously began beating. Cardiomyocytes expressed TnTc, MEF2C, MYL2A, MYHCβ, and NKX2.5. Stem cell-associated genes will be downregulated after differentiation.

Teratoma Formation: iPSCs injected into immunodeficient mice may spontaneously formed teratomas after certain time, such as nine weeks. Teratomas are tumors of multiple lineages containing tissue derived from the three germ layers endoderm, mesoderm and ectoderm; this is unlike other tumors, which typically are of only one cell type. Teratoma formation is a landmark test for pluripotency.

Embryoid Body: hESCs in culture spontaneously form ball-like embryo-like structures termed "embryoid bodies," which consist of a core of mitotically active and differentiating hESCs and a periphery of fully differentiated cells from all three germ layers. iPSCs may also form embryoid bodies and have peripheral differentiated cells.

Blastocyst Injection: hESCs naturally reside within the inner cell mass (embryoblast) of blastocysts, and in the embryoblast, differentiate into the embryo while the blastocyst's shell (trophoblast) differentiates into extraembryonic tissues. The hollow trophoblast is unable to form a living embryo, and thus it is necessary for the embryonic stem cells within the embryoblast to differentiate and form the embryo. iPSCs injected by micropipette into a trophoblast to generate a blastocyst transferred to recipient females, may result in chimeric living mouse pups: mice with iPSC derivatives incorporated all across their bodies with 10%-90 and chimerism.

ii. Epigenetic Reprogramming

Promoter Demethylation: Methylation is the transfer of a methyl group to a DNA base, typically the transfer of a methyl group to a cytosine molecule in a CpG site (adjacent cytosine/guanine sequence). Widespread methylation of a gene interferes with expression by preventing the activity of expression proteins or recruiting enzymes that interfere with expression. Thus, methylation of a gene effectively silences it by preventing transcription. Promoters of pluripotency-associated genes, including Oct-3/4, Rex1, and Nanog, may be demethylated in iPSCs, showing their promoter activity and the active promotion and expression of pluripotency-associated genes in iPSCs.

Histone Demethylation: Histones are compacting proteins that are structurally localized to DNA sequences that can effect their activity through various chromatin-related modifications. H3 histones associated with Oct-3/4, Sox-2, and Nanog may be demethylated to activate the expression of Oct-3/4, Sox-2, and Nanog.

B. Selection for Residue Free Feature

A reprogramming vector such as oriP-based plasmid in this invention will replicate extra-chromosomally and lose it presence in host cells after generations. However, an additional selection step for progeny cells essentially free of exogenous vector elements may facilitate this process. For example, a sample of progeny cell may be extracted to test the presence or loss of exogenous vector elements as known in the art (Leight and Sugden, Molecular and Cellular Biology, 2001).

A reprogramming vector may further comprise a selection marker, more specifically, a negative selection marker, such a gene encoding a thymidine kinase to select for progeny cells essentially free of such a selection marker. The human herpes simplex virus thymidine kinase type 1 gene (HSVtk) acts as a conditional lethal marker in mammalian cells. The HSVtk-encoded enzyme is able to phosphorylate certain nucleoside analogs (e.g., ganciclovir, an antiherpetic drug), thus converting them to toxic DNA replication inhibitors. An alternative or complementary approach is to test the absence of exogenous genetic elements in progeny cells, using conventional methods, such as RT-PCR, PCR, FISH (Fluorescent in situ hybridization), gene array, or hybridization (e.g., Southern blot).

VII. Culturing of iPS Cells

After somatic cells are introduced with a reprogramming vector using the disclosed methods, these cells may be cultured in a medium sufficient to maintain the pluripotency. Culturing of induced pluripotent stem (iPS) cells generated in this invention can use various medium and techniques developed to culture primate pluripotent stem cells, more specially, embryonic stem cells, as described in U.S. Pat. App. 20070238170 and U.S. Pat. App. 20030211603.

For example, like human embryonic stem (hES) cells, iPS cells can be maintained in 80% DMEM (Gibco #10829-018 or #11965-092), 20% defined fetal bovine serum (FBS) not heat inactivated, 1% non-essential amino acids, 1 mM L-glutamine, and 0.1 mM .beta.-mercaptoethanol. Alternatively, ES cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM .beta.-mercaptoethanol. Just before use, human bFGF is added to a final concentration of .about. 4 ng/mL (WO 99/20741).

IPS cells, like ES cells, have characteristic antigens that can be identified by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., in Robertson E, ed. Teratocarcinomas and Embryonic Stem Cells. IRL Press, 207-246, 1987). Pluripotency of embryonic stem cells can be confirmed by injecting approximately 0.5-10 10 6 cells into the rear leg muscles of 8-12 week old male SCID mice. Teratomas develop that demonstrate at least one cell type of each of the three germ layers.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of a Residue-Free Reprogramming Plasmid

Figure 3:
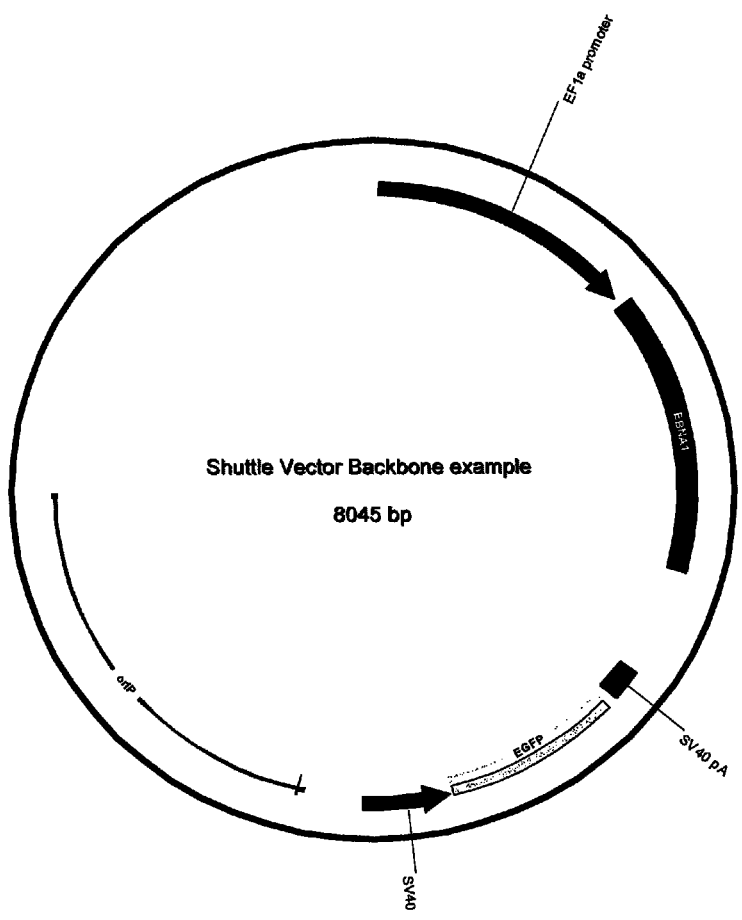
FIG. 3: An illustrative example of a recipient backbone plasmid used in the present invention.

The inventors construct a recipient backbone plasmid which contains the oriP sequence including DS and FR separated by approximately 1,000 base pairs derived from EBV (see Lindner and Sugden, 2007) and the abbreviated form of wild-type EBNA1 known as deltaUR1 (referred to as Dom-Neg2 in Kennedy et al. 2003) (FIG. 3). The plasmid is currently built to express deltaUR1 driven by the elongation factor 1a (EF1a) promoter which also contains an intronic sequence to maximize the expression of deltaUR1. The backbone plasmid has been currently set up to include a selection marker for mammalian cells encoding resistance to Hygromycin; however, the choice of resistance marker remains flexible according to the sensitivity of the cell line in which the plasmid will be introduced. Similarly, the plasmid encodes drug-resistance for prokaryotic selection and, in this case, the plasmid encodes resistance to ampicillin.

Figure 4:
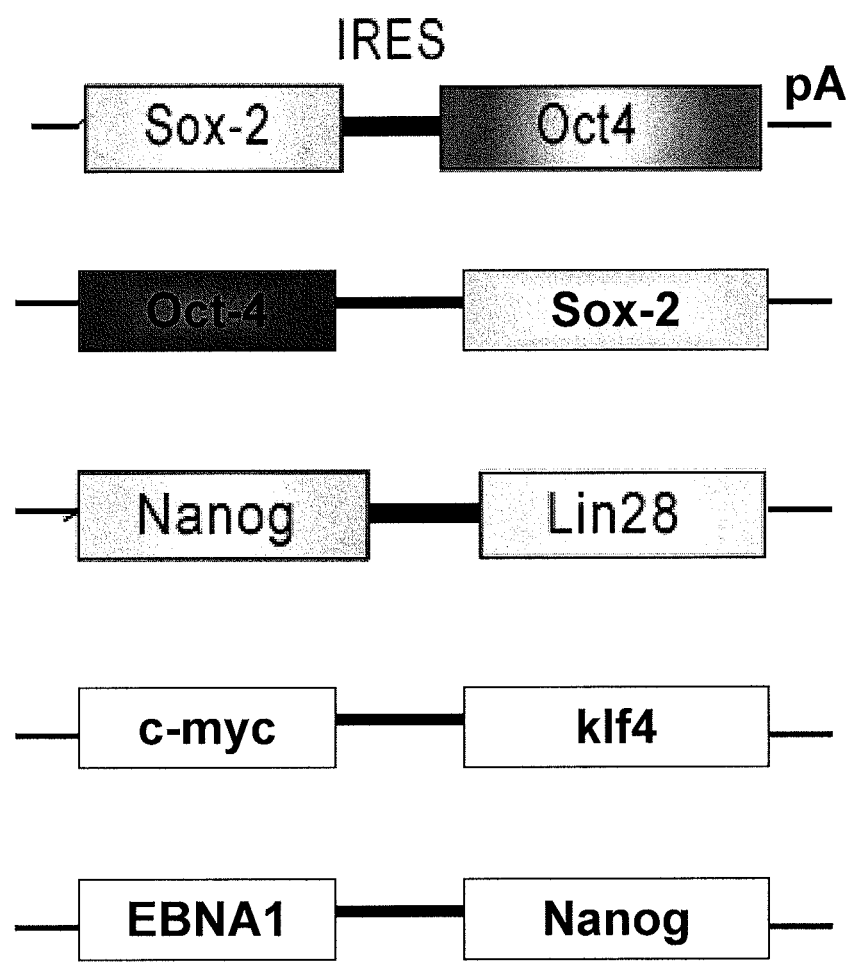

The inventors integrated a number of cassettes within the recipient plasmid described above that encode the genes required for and contribute to reprogramming cells to become pluripotent (i.e., iPS cells). One cassette encoded two genes essential for the reprogramming process, Sox-2 and Oct-4 (FIG. 4). The inventors could use the phosphoglycerate kinase (PGK) promoter, cytomegalovirus immediate-early gene (CMV) promoter or SV40 promoter to drive the expression of Sox-2 and Oct-4 but this choice is subject to change depending on the efficiency of that expression. Optionally, they have also included the second intron from the human beta-globin gene to also maximize expression of the transcript. Both genes, therefore, were encoded by the same transcript while translation could be initiated from a canonical ATG for Sox-2 and an internal ribosome entry site (IRES) derived from the encephalomyocarditis virus for Oct-4. Similarly, other cassettes encoded a bicistronic transcript encoding Nanog and Lin28 or encoded a bicistronic transcript encoding Klf4 and c-Myc (which were driven by the PGK promoter or any other suitable promoter) and separated by an IRES as well (FIG. 4). Variations of a multi-cistronic transcript comprising any two or more of Sox-2, Oct-4, Nanog, Lin28, Klf4, c-Myc, EBNA-1 could be used.

There could be certain variations of the system to optimize its efficiency. Current literature indicates that Lin28 may be dispensable for the reprogramming process and therefore it is likely that the inventors could adjust this plasmid system to include only Sox-2, Oct-4, and Nanog. Furthermore, the type of IRES chosen has been proven functional albeit in the context of other gene sets. However, it is possible that the IRES may prove inadequate to promote the levels of expression required for proper reprogramming and may result in breaking the cassettes up such that each reprogramming gene will be driven by its own human promoter.

Figure 5:
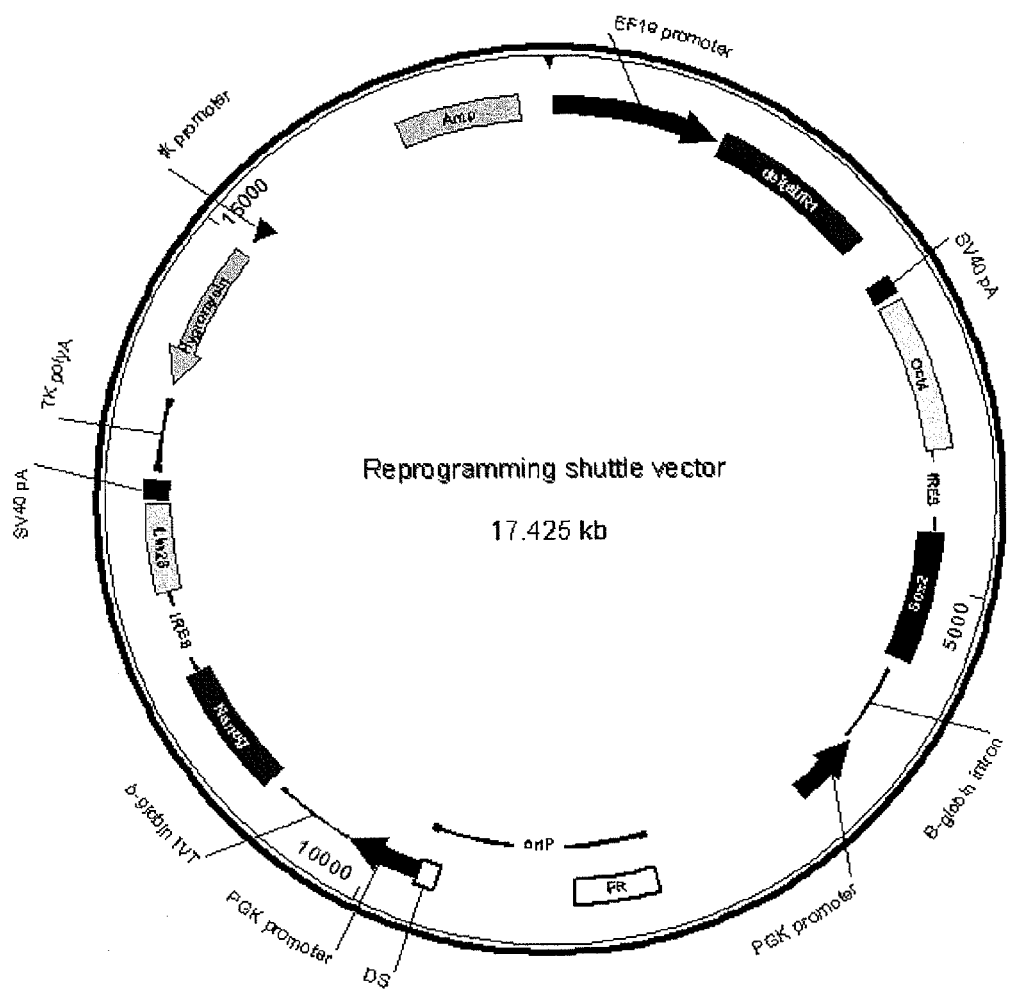
FIG. 5: An illustrative example of a reprogramming plasmid encoding Sox-2, Oct-4, Nanog and Lin28 (optionally).

In summary, the master shuttling plasmid or reprogramming plasmid could encode Sox-2, Oct-4, Nanog, and possibly Lin28 (FIG. 5) while its replication and maintenance could be promoted by the presence of oriP and deltaUR1. This plasmid will also be poised for future modifications to include a negative selection marker such as thymidine kinase and an additional positive selection marker such as sequences encoding green or red fluorescent protein.

Example 2

Use of a Residue-Free Reprogramming Plasmid

Successful reprogramming will depend on the efficient introduction of this large (15-20 kb) plasmid into mammalian cells. The inventors are currently employing a lypophyllic-based approach to introduce the DNA into human fibroblasts; however, this approach is likely to be modified according to the cell type being transfected. For example, they would likely chose electroporation for the introduction of DNA plasmids into hematopoietic cells. Once cells are properly transfected, the inventors will place these cells on a bed of irradiated mouse embryonic fibroblasts (MEFs) or matrigel on 10 cm culture dishes using media suitable for the transfected cells. Approximately six days following transfection, the media will be changed to media specialized for reprogramming cells and replaced daily to every other day (Yu et al, 2007).

Based on our current method of generating iPS cells, the inventors will likely select colonies resembling stem cells around twenty days post-transfection and transfer them to MEFs or matrigel in 6 well culture plates while feeding daily or every other day with specialized media. Once sufficient expansion has taken place, clones will be karyotyped and tested for proper markers specific to stem cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 4,684,611
U.S. Pat. No. 4,952,500
U.S. Pat. No. 5,302,523
U.S. Pat. No. 5,384,253
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
U.S. Patent Appln. 20030211603
U.S. Patent Appln. 20070238170
Adams, *J. Virol.*, 61(5):1743-1746, 1987.
Aiyar et al., *EMBO J.*, 17(21):6394-6403, 1998.
Alexander et al., *Proc. Nat. Acad. Sci. USA*, 85:5092-5096, 1988.
Almquist et al., *Med. Chem.*, 23(12):1392-1398, 1980.
Altmann et al., *Proc. Natl. Acad. Sci. USA*, 103(38):14188-14193, 2006.
Andrews et al., In: *Teratocarcinomas and Embryonic Stem Cells*, Robertson (Ed.), IRL Press, 207-246, 1987.
Aravind and Landsman, *Nucleic Acids Res.*, 26(19):4413-4421, 1998.
Ausubel et al., *Current Protocols in Molecular Biology*, Greene Publ. Assoc. Inc. & John Wiley & Sons, Inc., MA, 1994.
Baer et al., *Biochemistry*, 39:7041-7049, 2000.
Baer et al., *Nature*, 310(5974):207-211, 1984.
Bingham, *Cell*, 90(3):385-387, 1997.
Bochkarev et al., *Cell*, 84(5):791-800, 1996.
Bode et al., *Biol. Chem.*, 381:801-813, 2000b.
Bode et al., *Gene Ther. Mol. Biol.*, 6:33-46, 2001.
Bode et al., *Science*, 255(5041):195-197, 1992.
Boyer et al., *Cell*, 122(6):947-56, 2005.
Brambrink et al., *Cell Stem Cell*, 7(2):151-159, 2008.
Carbonelli et al., *FEMS Microbiol. Lett.*, 177(1):75-82, 1999.
Chambers et al., *Cell*, 113(5):643-55, 2003.
Chandler et al., *Proc. Natl. Acad. Sci. USA*, 94(8):3596-601, 1997.
Chaudhuri et al., *Proc. Natl. Acad. Sci. USA*, 98(18):10085-10089, 2001.
Chen and Okayama, *Mol. Cell Biol.*, 7(8):2745-2752, 1987.
Cocea, *Biotechniques*, 23(5):814-816, 1997.
Dhar et al., *Cell*, 106(3):287-296, 2001.
EPO 0273085
EPO 45665
Ercolani et al., *J. Biol. Chem.*, 263: 15335-15341, 1988.
Ermakova et al., *J. Biol. Chem.*, 271(51):33009-33017, 1996.
Evans, et al., In: *Cancer Principles and Practice of Oncology*, Devita et al. (Eds.), Lippincot-Raven, NY, 1054-1087, 1997.
Fechheimer et al., *Proc Natl. Acad. Sci. USA*, 84:8463-8467, 1987.
Fischer et al., *J. Virol.*, 71:5148-5146, 1997.
Fraley et al., *Proc. Natl. Acad. Sci. USA*, 76:3348-3352, 1979.
Frappier and O'Donnell, *Proc. Natl. Acad. Sci. USA*, 88(23):10875-10879, 1991.
Gahn and Schildkraut, *Cell*, 58(3):527-535, 1989.
Gahn and Sugden, *J. Virol.*, 69(4):2633-2636, 1995.
Garrick et al., *Nat. Genet.*, 18:56-59, 1998.
Ghosh and Bachhawat Gopal, 1985
Gopal, *Mol. Cell Biol.*, 5:1188-1190, 1985.
Graham and Van Der Eb, *Virology*, 52:456-467, 1973.
Hann, *J. Chem. Soc. Perkin Trans., I* 307-314, 1982.
Harland and Weintraub, *J. Cell Biol.*, 101(3):1094-1099, 1985.
Hegde et al., *Nature*, 359(6395):505-512, 1992.
Holladay et al., *Tetrahedron. Lett.*, 24:4401-4404, 1983.
Hruby, *Life Sci.*, 31:189-199, 1982.
Hudson et al., *Int. J. Pept. Prot. Res.*, 14:177-185, 1979.
Hung et al., *Proc. Natl. Acad. Sci. USA*, 98(4):1865-1870, 2001.
Jenke et al., *Proc. Natl. Acad. Sci. USA*, 101 (31), 11322-11327, 2004.
Jennings-White et al., *Tetrahedron Lett.*, 23:2533, 1982.
Julien et al., *Virology*, 326(2):317-328, 2004.
Kaeppler et al., *Plant Cell Reports*, 9:415-418, 1990.
Kanda et al., *Mol. Cell. Biol.*, 21(10):3576-3588, 2001.
Kaneda et al., *Science*, 243:375-378, 1989.
Karin et al., *Cell*, 36:371-379, 1989.
Kato et al, *J. Biol. Chem.*, 266:3361-3364, 1991.
Kennedy and Sugden, *Mol. Cell. Biol.*, 23(19):6901-6908, 2003.
Kennedy et al., *Proc. Natl. Acad. Sci. USA*, 100:14269-14274, 2003.
Kim et al., *J. Biol. Chem.*, 275(40):31245-31254, 2000.
Kim et al., *Virology*, 239(2):340-351, 1997.
Kirchmaier and Sugden, *J. Virol.*, 69(2):1280-1283, 1995.
Kirchmaier and Sugden, *J. Virol.*, 71(3):1766-1775, 1997.
Kirchmaier and Sugden, *J. Virol.*, 72(6):4657-4666, 1998.
Klein et al., *Nature*, 327:70-73, 1987.
Langle-Rouault et al., *J. Virol.*, 72(7):6181-6185, 1998.
Leight and Sugden, *Mol. Cell Bio.*, 21:4149-61, 2001.
Levenson et al., *Hum. Gene Ther.*, 9(8):1233-1236, 1998.
Levitskaya et al., *Nature*, 375(6533):685-688, 1995.
Levitskaya et al., *Proc. Natl. Acad. Sci. USA*, 94(23):12616-12621, 1997.
Lindner and Sugden, *Plasmid*, 58:1-12, 2007.
Lindner et al., *J. Virol.*, 82(12):5693-702, 2008.
Macejak and Sarnow, *Nature*, 353:90-94, 1991.
Mackey and Sugden, *Mol. Cell. Biol.*, 19(5):3349-3359, 1999.
Mackey et al., *J. Virol.*, 69(10):6199-6208, 1995.
Maniatis, et al., *Molecular Cloning, A Laboratory Manual*, Cold Spring Harbor Press, Cold Spring Harbor, N.Y., 1988.
Manzini et al., *Proc. Natl. Acad. Sci. USA*, 103(47):17672-17677, 2006.
Marechal et al., *J. Virol*, 73(5):4385-4392, 1999.
Middleton and Sugden, *J. Virol.*, 66(1):489-495, 1992.
Morley, *Trends Pharm. Sci.*, 463-468, 1980.
Nabel et al., *Science*, 244(4910):1342-1344, 1989.
Nanbo and Sugden, *EMBO J.*, 26:4252-62, 2007.
Ng, *Nuc. Acid Res.*, 17:601-615, 1989.

Nicolau and Sene, *Biochim. Biophys. Acta*, 721:185-190, 1982.
Nicolau et al., *Methods Enzymol.*, 149:157-176, 1987.
Niller et al., *J. Biol. Chem.*, 270(21):12864-12868, 1995.
Omirulleh et al., *Plant Mol. Biol.*, 21(3):415-428, 1993.
Pelletier and Sonenberg, *Nature*, 334(6180):320-325, 1988.
Perales et al., *Proc. Natl. Acad. Sci. USA*, 91:4086-4090, 1994.
Piechaczek et al., *Nucleic Acids Res.*, 27(2):426-428, 1999.
Potrykus et al., *Mol. Gen. Genet.*, 199(2):169-177, 1985.
Potter et al., *Proc. Natl. Acad. Sci. USA*, 81:7161-7165, 1984.
Quitsche et al., *J. Biol. Chem.*, 264:9539-9545, 1989.
Rawlins et al., *Cell*, 42((3):859-868, 1985.
Reisman and Sugden, *Mol. Cell. Biol.*, 6(11):3838-3846, 1986.
Reisman et al., *Mol. Cell. Biol.*, 5(8):1822-1832, 1985.
Richards et al., *Cell*, 37:263-272, 1984.
Rippe, et al., *Mol. Cell Biol.*, 10:689-695, 1990.
Ritzi et al., *J. Cell Sci.*, 116(Pt 19):3971-3984, 2003.
Sambrook et al., In: *Molecular cloning: a laboratory manual*, 2$^{nd}$ Ed., Cold Spring Harbor Laboratory Press, Cold Spring Harbor, N.Y., 1989.
Schaarschmidt et al., *EMBO J.*, 23(1):191-201, 2004.
Schepers et al., *EMBO J.*, 20(16):4588-4602, 2001.
Sears et al., *J. Virol.*, 77(21):11767-11780, 2003.
Sears et al., *J. Virol.*, 78(21):11487-11505, 2004.
Shire et al., *J. Virol.*, 73(4):2587-2595, 1999.
Spatola et al., *Life Sci.*, 38:1243-1249, 1986.
Spatola, In: *Peptide Backbone Modifications*, 1:3, 1983.
Spatola, In: *Chemistry and Biochemistry of Amino Acids, Peptides, and Proteins*, Weinstein (Ed.), Marcel Dekker, NY, 267, 1983.
Stadtfeld et al., *Cell Stem Cell*, 2:230-240, 2008.
Su et al., *Proc. Natl. Acad. Sci. USA*, 88(23):10870-19874, 1991.
Sugden and Warren, *J. Virol.*, 63(6):2644-2649, 1989.
Takahashi et al., *Cell*, 126(4):663-676, 2006.
Takahashi et al., *Cell*, 126(4):663-76, 2007.
Torchia et al., *Curr. Opin. Cell Biol.*, 10:373-383, 1998.
Tur-Kaspa et al., *Mol. Cell Biol.*, 6:716-718, 1986.
Wagner et al., *Proc. Natl. Acad. Sci. USA* 87(9):3410-3414, 1990.
Wang et al., *Mol. Cell. Biol.*, 26(3):1124-1134, 2006.
Wilson et al., *Science*, 244:1344-1346, 1989.
WO 94/09699
WO 95/06128
WO 99/20741
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Wu et al., *J. Virol.*, 76(5):2480-2490, 2002.
Wysokenski and Yates, *J. Virol.*, 63(6):2657-2666, 1989.
Yamanaka et al., *Cell*, 131(5):861-72, 2007.
Yang and Russell, *Proc. Natl. Acad. Sci. USA*, 87:4144-4148, 1990.
Yates and Guan, *J. Virol.*, 65(1):483-488, 1991.
Yates et al., *J. Virol.*, 74(10):4512-4522, 2000.
Yates et al., *Nature*, 313:812-815, 1985.
Yates et al., *Proc. Natl. Acad. Sci. USA*, 81:3806-3810, 1984.
Yates, *Cancer Cells*, (6)197-205, 1988.
Yin et al., *Science*, 301(5638):1371-1374, 2003.
Yu et al., *Science*, 318:1917-1920, 2007.
Zhou et al., *EMBO J.*, 24(7):1406-1417, 2005.

What is claimed is:

1. A method of producing human induced pluripotent stem (iPS) cells population and having cells that are essentially free of differentiation programming vector genetic elements, the method comprising the steps of:
   a) obtaining a starting population of human somatic cells;
   b) obtaining one or more iPS reprogramming vectors comprising an OriP replication origin and one or more expression cassettes encoding iPS reprogramming factors wherein one or more of said expression cassettes comprise a nucleotide sequence encoding EBNA-1 of EBV, or a derivative thereof which has a deletion of residues corresponding to residues 65 to 89 of EBNA-1, and/or a deletion of residues corresponding to residues 90 to 328 of EBNA-1;
   c) introducing the iPS reprogramming vector(s) into the human somatic cells;
   d) culturing the human somatic cells that comprise the iPS reprogramming vector(s) to effect expression of said reprogramming factors such that traits consistent with embryonic stem cells arise in at least a portion of cells in the cultured cells; and
   e) further culturing cells having the embryonic stem cell traits for a sufficient number of generations in the absence of positive selection for the presence of the iPS reprogramming vector(s) to provide human iPS cells that are essentially free of iPS reprogramming vector genetic elements.

2. The method of claim 1, wherein cells of the starting cell population are fibroblasts, keratinocytes, hematopoietic cells, mesenchymal cells, liver cells, stomach cells, or β cells.

3. The method of claim 1, wherein the iPS reprogramming factors comprise Sox-2 and Oct-4.

4. The method of claim 3, wherein the reprogramming factors further comprise Nanog or Lin28.

5. The method of claim 1, further comprising a step of differentiating the human iPS cells provided in step e).

* * * * *

```
                        SEQUENCE LISTING

<160> NUMBER OF SEQ ID NOS: 4

<210> SEQ ID NO 1
<211> LENGTH: 641
<212> TYPE: PRT
<213> ORGANISM: Human herpesvirus 4

<400> SEQUENCE: 1

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
                20                  25                  30

Arg Arg Gly Gly Asp Asn His Gly Arg Gly Arg Gly Arg Gly Arg Gly
            35                  40                  45

Arg Gly Gly Gly Arg Pro Gly Ala Pro Gly Gly Ser Gly Ser Gly Pro
        50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Gly
                100                 105                 110

Gly Gly Ala Gly Gly Ala Gly Gly Ala Gly Gly Ala Gly Ala Gly Gly
            115                 120                 125

Gly Ala Gly Ala Gly Gly Gly Ala Gly Gly Ala Gly Gly Ala Gly Ala
        130                 135                 140
```

```
Gly Gly Gly Ala Gly Ala Gly Gly Ala Gly Ala Gly Ala Gly
145                 150                 155                 160
Gly Gly Ala Gly Ala Gly Gly Ala Gly Ala Gly Gly Ala Gly
                165                 170                 175
Ala Gly Gly Ala Gly Gly Ala Gly Ala Gly Gly Ala Gly Gly
            180                 185                 190
Ala Gly Gly Ala Gly Ala Gly Gly Ala Gly Ala Gly Gly Ala Gly
        195                 200                 205
Gly Ala Gly Gly Ala Gly Ala Gly Gly Ala Gly Ala Gly Gly Ala
    210                 215                 220
Gly Gly Ala Gly Gly Ala Gly Ala Gly Gly Ala Gly Ala Gly Ala
225                 230                 235                 240
Gly Ala Gly Gly Ala Gly Ala Gly Gly Ala Gly Ala Gly Ala Gly
            245                 250                 255
Gly Ala Gly Gly Ala Gly Ala Gly Gly Ala Gly Ala Gly Ala Gly
            260                 265                 270
Gly Gly Ala Gly Gly Ala Gly Ala Gly Gly Ala Gly Ala Gly Ala
        275                 280                 285
Ala Gly Gly Ala Gly Gly Ala Gly Ala Gly Gly Ala Gly Ala Gly
290                 295                 300
Ala Gly Gly Ala Gly Gly Ala Gly Ala Gly Gly Ala Gly Ala Gly
305                 310                 315                 320
Gly Ala Gly Ala Gly Gly Gly Arg Gly Arg Gly Ser Gly Gly
                325                 330                 335
Arg Gly Arg Gly Gly Ser Gly Gly Arg Gly Arg Gly Ser Gly Gly
            340                 345                 350
Arg Arg Gly Arg Gly Arg Glu Arg Ala Arg Gly Gly Ser Arg Glu Arg
        355                 360                 365
Ala Arg Gly Arg Gly Arg Gly Arg Gly Glu Lys Arg Pro Arg Ser Pro
    370                 375                 380
Ser Ser Gln Ser Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
            420                 425                 430
Ala Ile Glu Gln Gly Pro Ala Asp Asp Pro Gly Glu Gly Pro Ser Thr
        435                 440                 445
Gly Pro Arg Gly Gln Gly Asp Gly Gly Arg Arg Lys Lys Gly Gly Trp
    450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
            500                 505                 510
Ser Lys Thr Ser Leu Tyr Asn Leu Arg Arg Gly Thr Ala Leu Ala Ile
        515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
```

```
Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
            595                 600                 605

Trp Phe Pro Pro Met Val Glu Gly Ala Ala Ala Glu Gly Asp Asp Gly
    610                 615                 620

Asp Asp Gly Asp Glu Gly Gly Asp Gly Asp Glu Gly Glu Glu Gly Gln
625                 630                 635                 640

Glu

<210> SEQ ID NO 2
<211> LENGTH: 1926
<212> TYPE: DNA
<213> ORGANISM: Human herpesvirus 4

<400> SEQUENCE: 2
```

| | | | | |
|---|---|---|---|---|
| atgtctgacg | agggggccagg | tacaggacct | ggaaatggcc | taggagagaa | gggagacaca | 60 |
| tctggaccag | aaggctccgg | cggcagtgga | cctcaaagaa | gaggggggtga | taaccatgga | 120 |
| cgaggacggg | gaagaggacg | aggacgagga | ggcggaagac | caggagcccc | gggcggctca | 180 |
| ggatcagggc | caagacatag | agatggtgtc | cggagacccc | aaaaacgtcc | aagttgcatt | 240 |
| ggctgcaaag | ggacccacgg | tggaacagga | gcagagcag | gagcgggagg | ggcaggagca | 300 |
| ggaggggcag | gagcaggagg | aggggcagga | gcaggaggag | gggcaggagg | ggcaggaggg | 360 |
| gcaggagggg | caggagcagg | aggaggggca | ggagcaggag | gaggggcagg | aggggcagga | 420 |
| ggggcaggag | caggaggagg | ggcaggagca | ggaggagggg | caggaggggc | aggagcagga | 480 |
| ggaggggcag | gaggggcagg | aggggcagga | gcaggaggag | gggcaggagc | aggaggaggg | 540 |
| gcaggagggg | caggagcagg | aggaggggca | ggaggggcag | gaggggcagg | agcaggagga | 600 |
| ggggcaggag | caggaggggc | aggaggggca | ggaggggcag | gagcaggagg | ggcaggagca | 660 |
| ggaggagggg | caggaggggc | aggaggggca | ggagcaggag | gggcaggagc | aggaggggca | 720 |
| ggagcaggag | gggcaggagc | aggaggggca | ggaggggcag | gagcaggagg | ggcaggaggg | 780 |
| gcaggagcag | gaggggcagg | aggggcagga | gcaggaggag | gggcaggagg | ggcaggagca | 840 |
| ggaggagggg | caggaggggc | aggagcagga | ggggcaggag | gggcaggagc | aggaggggca | 900 |
| ggaggggcag | gagcaggagg | ggcaggaggg | gcaggagcag | gaggaggggc | aggagcagga | 960 |
| ggggcaggag | caggaggtgg | aggccggggt | cgaggaggca | gtggaggccg | ggtcgagga | 1020 |
| ggtagtggag | gccggggtcg | aggaggtagt | ggaggccgcc | ggggtagagg | acgtgaaaga | 1080 |
| gccagggggg | gaagtcgtga | aagagccagg | gggagaggtc | gtggacgtgg | agaaaagagg | 1140 |
| cccaggagtc | ccagtagtca | gtcatcatca | tccgggtctc | caccgcgcag | gccccctcca | 1200 |
| ggtagaaggc | catttttcca | ccctgtaggg | gaagccgatt | attttgaata | ccaccaagaa | 1260 |
| ggtggcccag | atggtgagcc | tgacgtgccc | ccggagcga | tagagcaggg | ccccgcagat | 1320 |
| gacccaggag | aaggcccaag | cactggaccc | cggggtcagg | gtgatggagg | caggcgcaaa | 1380 |
| aaaggagggt | ggtttggaaa | gcatcgtggt | caaggaggtt | ccaacccgaa | atttgagaac | 1440 |
| attgcagaag | gttaagagc | tctcctggct | aggagtcacg | tagaaaggac | taccgacgaa | 1500 |
| ggaacttggg | tcgccggtgt | gttcgtatat | ggaggtagta | agacctccct | ttacaaccta | 1560 |
| aggcgaggaa | ctgcccttgc | tattccacaa | tgtcgtctta | caccattgag | tcgtctcccc | 1620 |
| tttggaatgg | cccctggacc | cggcccacaa | cctggcccgc | taaggagtc | cattgtctgt | 1680 |
| tatttcatgg | tctttttaca | aactcatata | tttgctgagg | ttttgaagga | tgcgattaag | 1740 |

```
gaccttgtta tgacaaagcc cgctcctacc tgcaatatca gggtgactgt gtgcagcttt    1800
gacgatggag tagatttgcc tccctggttt ccacctatgg tggaaggggc tgccgcggag    1860
ggtgatgacg gagatgacgg agatgaagga ggtgatggag atgagggtga ggaagggcag    1920
gagtga                                                               1926
```

<210> SEQ ID NO 3
<211> LENGTH: 392
<212> TYPE: PRT
<213> ORGANISM: Human herpesvirus 4

<400> SEQUENCE: 3

```
Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Ala
    50                  55                  60

Gly Ala Gly Ala Gly Ala Gly Gly Ala Gly Ala Gly Gly Gly Gly Arg
65                  70                  75                  80

Gly Arg Gly Gly Ser Gly Gly Arg Gly Arg Gly Gly Ser Gly Gly Arg
                85                  90                  95

Gly Arg Gly Gly Ser Gly Gly Arg Arg Gly Arg Gly Arg Glu Arg Ala
            100                 105                 110

Arg Gly Gly Ser Arg Glu Arg Ala Arg Gly Arg Gly Arg Gly Arg Gly
        115                 120                 125

Glu Lys Arg Pro Arg Ser Pro Ser Ser Gln Ser Ser Ser Ser Gly Ser
    130                 135                 140

Pro Pro Arg Arg Pro Pro Gly Arg Arg Pro Phe Phe His Pro Val
145                 150                 155                 160

Gly Glu Ala Asp Tyr Phe Glu Tyr His Gln Glu Gly Gly Pro Asp Gly
                165                 170                 175

Glu Pro Asp Val Pro Pro Gly Ala Ile Glu Gln Gly Pro Ala Asp Asp
            180                 185                 190

Pro Gly Glu Gly Pro Ser Thr Gly Pro Arg Gly Gln Gly Asp Gly Gly
        195                 200                 205

Arg Arg Lys Lys Gly Gly Trp Phe Gly Lys His Arg Gly Gln Gly Gly
    210                 215                 220

Ser Asn Pro Lys Phe Glu Asn Ile Ala Glu Gly Leu Arg Ala Leu Leu
225                 230                 235                 240

Ala Arg Ser His Val Glu Arg Thr Thr Asp Glu Gly Thr Trp Val Ala
                245                 250                 255

Gly Val Phe Val Tyr Gly Gly Ser Lys Thr Ser Leu Tyr Asn Leu Arg
            260                 265                 270

Arg Gly Thr Ala Leu Ala Ile Pro Gln Cys Arg Leu Thr Pro Leu Ser
        275                 280                 285

Arg Leu Pro Phe Gly Met Ala Pro Gly Pro Gly Pro Gln Pro Gly Pro
    290                 295                 300

Leu Arg Glu Ser Ile Val Cys Tyr Phe Met Val Phe Leu Gln Thr His
305                 310                 315                 320

Ile Phe Ala Glu Val Leu Lys Asp Ala Ile Lys Asp Leu Val Met Thr
                325                 330                 335
```

```
Lys Pro Ala Pro Thr Cys Asn Ile Arg Val Thr Val Cys Ser Phe Asp
                340                 345                 350

Asp Gly Val Asp Leu Pro Pro Trp Phe Pro Pro Met Val Glu Gly Ala
            355                 360                 365

Ala Ala Glu Gly Asp Asp Gly Asp Asp Gly Asp Glu Gly Gly Asp Gly
    370                 375                 380

Asp Glu Gly Glu Glu Gly Gln Glu
385                 390

<210> SEQ ID NO 4
<211> LENGTH: 1179
<212> TYPE: DNA
<213> ORGANISM: Human herpesvirus 4

<400> SEQUENCE: 4
atgtctgacg aggggccagg tacaggacct ggaaatggcc taggagagaa gggagacaca    60
tctggaccag aaggctccgg cggcagtgga cctcaaagaa gaggggggtga taaccatgga   120 cgaggacggg gaagaggacg aggacgagga ggcggaagac caggagcccc gggcggctca   180
ggatcagggg ccggcgcagg agcaggagcg ggaggggcag gagcaggagg tggaggccgg   240
ggtcgaggag gcagtggagg ccggggtcga ggaggtagtg gaggccgggg tcgaggaggt   300
agtggaggcc gccggggtag aggacgtgaa agagccaggg ggggaagtcg tgaaagagcc   360 aggggggagag gtcgtggacg tggagaaaag aggcccagga gtcccagtag tcagtcatca   420
tcatccgggt ctccaccgcg caggcccccct ccaggtagaa ggccattttt ccaccctgta   480
ggggaagccg attattttga ataccaccaa gaaggtggcc cagatggtga gcctgacgtg   540
cccccgggag cgatagagca gggccccgca gatgacccag gagaaggccc aagcactgga   600
ccccggggtc agggtgatgg aggcaggcgc aaaaaaggag ggtggtttgg aaagcatcgt   660
ggtcaaggag gttccaaccc gaaatttgag aacattgcag aaggtttaag agctctcctg   720
gctaggagtc acgtagaaag gactaccgac gaaggaactt gggtcgccgg tgtgttcgta   780
tatggaggta gtaagacctc cctttacaac ctaaggcgag gaactgccct tgctattcca   840
caatgtcgtc ttacaccatt gagtcgtctc ccctttggaa tggcccctgg acccggccca   900
caacctggcc cgctaaggga gtccattgtc tgttatttca tggtcttttt acaaactcat   960
atatttgctg aggttttgaa ggatgcgatt aaggaccttg ttatgacaaa gcccgctcct  1020
acctgcaata tcagggtgac tgtgtgcagc tttgacgatg gagtagattt gcctccctgg  1080
tttccaccta tggtggaagg ggctgccgcg gagggtgatg acggagatga cggagatgaa  1140
ggaggtgatg gagatgaggg tgaggaaggg caggagtga                         1179
```